US010300048B2

(12) United States Patent
Reymond et al.

(10) Patent No.: US 10,300,048 B2
(45) Date of Patent: *May 28, 2019

(54) THIAZOLIDINONES AS CELLULAR ANANDAMIDE UPTAKE INHIBITORS AND THEIR USE IN THE TREATMENT OF PSYCHIATRIC OR NEUROLOGICAL DISORDERS AND INFLAMMATION, IN PARTICULAR NEUROINFLAMMATION

(71) Applicant: UNIVERSITAT BERN, Bern (CH)

(72) Inventors: Jean-Louis Reymond, Bulle (CH); Jurg Gertsch, Schaffhausen (CH); Simon Nicolussi, Staad (CH)

(73) Assignee: UNIVERSITAT BERN, Bern (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/314,105

(22) PCT Filed: May 28, 2015

(86) PCT No.: PCT/EP2015/061914
§ 371 (c)(1),
(2) Date: Nov. 28, 2016

(87) PCT Pub. No.: WO2015/181336
PCT Pub. Date: Dec. 3, 2015

(65) Prior Publication Data
US 2017/0296515 A1    Oct. 19, 2017

(30) Foreign Application Priority Data

May 28, 2014 (EP) .................................... 14170448
Jun. 3, 2014 (EP) .................................... 14171022

(51) Int. Cl.
*A61K 31/426* (2006.01)
*A61K 31/427* (2006.01)

(52) U.S. Cl.
CPC .......... *A61K 31/426* (2013.01); *A61K 31/427* (2013.01)

(58) Field of Classification Search
CPC ............................ A61K 31/426; A61K 31/427
See application file for complete search history.

(56) References Cited

U.S. PATENT DOCUMENTS

| 7,435,828 | B2 * | 10/2008 | Binkert | ................. | A61K 31/426 |
| | | | | | 548/184 |
| 8,273,779 | B2 * | 9/2012 | Binkert | ................. | A61K 31/426 |
| | | | | | 514/370 |
| 2017/0197952 | A1 * | 7/2017 | Reymond | ............. | C07D 417/06 |

FOREIGN PATENT DOCUMENTS

| CN | 101274918 | 10/2008 |
| CN | 101565408 | 10/2009 |
| WO | 2005/054215 | 6/2005 |
| WO | 2006/020680 | 2/2006 |
| WO | 2007/059195 | 5/2007 |
| WO | 2009/109998 | 9/2009 |
| WO | WO-2012/170839 A2 * | 12/2012 ......... A61K 31/4196 |

OTHER PUBLICATIONS

Chemical Abstracts Registry No. 664310-84-3, indexed in the Registry file on STN CAS Online on Mar. 18, 2004.*
Naeem et al., Pakistan Journal of Pharmaceutical Sciences, Oct. 2012, 25(4), pp. 731-739.*
An English translation of CN 101274918 A, Wang et al., 2008.*
Tanveer et al., WIREs Membrane Transport and Signaling, Sep./Oct. 2012, vol. 1, pp. 633-639 (Year: 2012).*
Koppel et al., Journal of Alzheimers Disease, Nov. 2008; 15(3), pp. 495-504 (Year: 2008).*
An English Human translation of CN 101274918 A (Wang et al.), 2008. (Year: 2008).*
Carson et al., Clinical Neuroscience Research, 6(5), 2006, pp. 237-245. (Year: 2006).*
Ottana R et al: "5-Arylidene-2-imino-4-thiazolidinones: Design and synthesis of novel anti-inflammatory agents", Bioorganic & Medicinal Chemistry, Pergamon, GB, vol. 13, No. 13, Jul. 1, 2005, pp. 4243-4252.
L. Piali et al: "The Selective Sphingosine 1-Phosphate Receptor 1 Agonist Ponesimod Protects against Lymphocyte-Mediated Tissue Inflammation", Journal of Pharmacology and Experimental Therapeutics, vol. 337, No. 2, Feb. 23, 2011, pp. 547-556.
Adel Hamza et al: "Novel human mPGES-1 inhibitors identified through structure-based virtual screening", Bioorganic & Medicinal Chemistry, Pergamon, GB, vol. 19, No. 20, Aug. 18, 2011 pp. 6077-6086.
Loria F et al:"An endocannabinoid tone limits excitotoxicity in vitro and in a Model of multiple sclerosis", Neurobiology of Disease, Blackwell Scientific Publications, Oxford, GB, vol. 37, No. 1, Jan. 1, 2010, pp. 166-176.
Ashton et al. "Endocannabinoid system dysfunction in mood and related disorders" Acta Psychiatr Scand 2011: 124: 250-261.
Aso et al. "Cannabinoids for treatment of Alzheimer's disease: moving toward the clinic" Frontiers in Pharm. 5: Article 37, 2014 (11 pages).
Berger et al "Targeting Fatty Acid Binding Protein (FABP) AnandamideTransporters—A Novel Strategy for Development of Anti-Inflammatory and Anti-Nociceptive Drugs" PLOS One; Dec. 2012 | vol. 7 | Issue 12, 12 pages.
Boll, "2-Imino-thiazolidin-4-one Derivatives as Potent, Orally Active S1P1 Receptor Agonists" J. Med. Chem. 2010, 53, 4198-4211.
Chicca, "Evidence for Bidirectional Endocannabinoid Transport across Cell Membranes" The Journal of Biological Chemistry vol. 287, No. 41, pp. 34660-34682, Oct. 5, 2012.
Chicca, "Functionalization of β-Caryophyllene Generates Novel Polypharmacology in the Endocannabinoid System" ACS Chem. Biol. 2014, 9, 1499-1507.

(Continued)

Primary Examiner — Laura L Stockton
(74) Attorney, Agent, or Firm — JMB DAVIS BEN-DAVID

(57) ABSTRACT

The invention relates to a compound comprising the following general formula (1) for use in the treatment of psychiatric or neurological disorders and inflammation, in particular neuroinflammation: (1) wherein each of R1, R2 and R3 are selected independently from each other from alkyl, alkoxy, alkenyl, alkynyl, cycloalkyl, aryl, heterocycle or heteroaryl.

4 Claims, 5 Drawing Sheets

(56) References Cited

OTHER PUBLICATIONS

Figure 1:
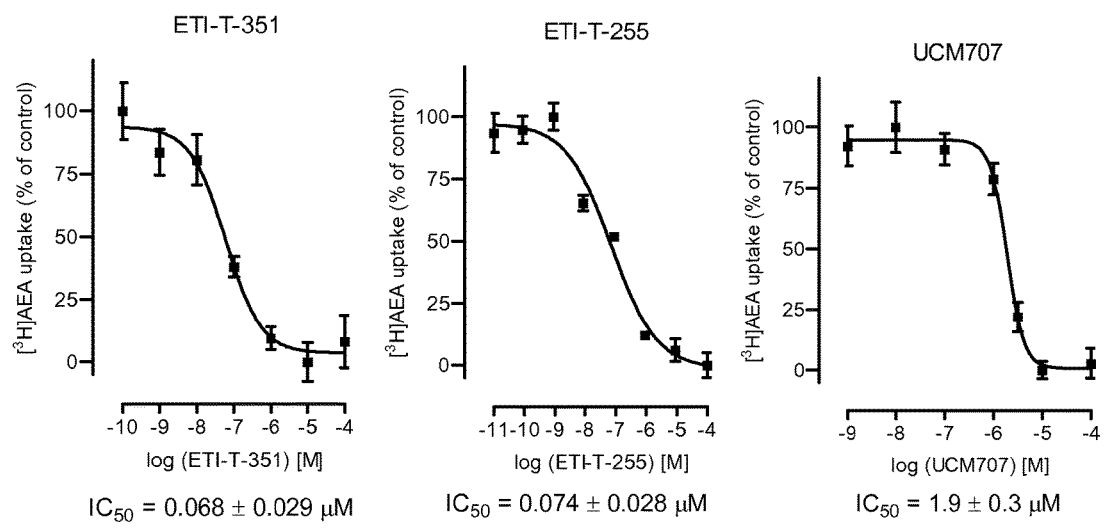

Correa, "The Endocannabinoid Anandamide:From Immunomodulation to Neuroprotection. Implications for Multiple Sclerosis" Vitamins and Hormones, vol. 81, Elsevier, 2009, 207-230.
De Lago "UCM707, an inhibitor of the anandamide uptake, behaves as a symptom control agent in models of Huntington's disease and multiple sclerosis, but fails to delay/arrest the progression of different motor-related disorders" European Neuropsychopharmacology (2006) 16, 7-18.
Fowler "Selective inhibition of anandamide cellular uptake versus enzymatic hydrolysis—a difficult issue to handle" European Journal of Pharmacology 492 (2004) 1-11.
Fowler "Transport of endocannabinoids across the plasma membrane and within the cell" FEBS Journal 280 (2013) 1895-1904.
Hasanein "Effects of the Endocannabinoid Transport Inhibitors AM404 and UCM707 on Diabetic Neuropathy in Rats" Clinical and Experimental Pharmacology and Physiology (2009) 36, 1127-1131.
Hofmann, "Marijuana, endocannabinoids, and epilepsy: Potential and challenges for improved therapeutic intervention" Experimental Neurology 244 (2013) 43-50.
Kaczocha "Inhibition of Fatty Acid Binding Proteins Elevates Brain Anandamide Levels and Produces Analgesia" PLOS One Apr. 2014 | vol. 9 | Issue 4, 10 pages.
Lopez-Rodriguez "Design, Synthesis and Biological Evaluation of Novel Arachidonic Acid Derivatives as Highly Potent and Selective Endocannabinoid Transporter Inhibitors" J. Med. Chem. 2001, 44, 4505-4508.
Lopez-Rodriguez "Design, synthesis and biological evaluation of new endocannabinoid transporter inhibitors" European Journal of Medicinal Chemistry 38 (2003) 403-412.
Loría, "An endocannabinoid tone limits excitotoxicity in vitro and in a model of multiple sclerosis" Neurobiology of Disease 37 (2010) 166-176.
Marsicano "CB1 Cannabinoid Receptors and On-Demand Defense Against Excitotoxicity" Science, 302: 84-88. 2003.
Murillo-Rodríguez, "The Anandamide Membrane Transporter Inhibitor, VDM-11, Modulates Sleep and c-Fos Expression in the Rat Brain" Neuroscience 157 (2008) 1-11.
Murillo-Rodríguez, "The administration of endocannabinoid uptake inhibitors OMDM-2 or VDM-11 promotes sleep and decreases extracellular levels of dopamine in rats" Physiology & Behavior 109 (2013) 88-95.
Nicolussi, "Guineensine is a novel inhibitor of endocannabinoid uptake showing cannabimimetic behavioral effects in BALB/c mice" Pharmacological Research 80 (2014) 52-65.
Nicolussi, "Endocannabinoid Transport Revisited" Vitamins and Hormones, vol. 98 2015 Elsevier pp. 441-485.
Ortar "Novel selective and metabolically stable inhibitors of anandamide cellular uptake" Biochemical Pharmacology 65 (2003) 1473-1481.
Ortega-Gutiérrez, "Activation of the endocannabinoid system as a therapeutic approach in a murine model of multiple sclerosis" The FASEB Journal express article 10.1096/fj.04-2464fje. Published online Jun. 7, 2005.
Pacher, "The Endocannabinoid System as an Emerging Target of Pharmacotherapy" Pharmacol Rev 58:389-462, 2006.
Scherma, "The anandamide transport inhibitor AM404 reduces the rewarding effects of nicotine and nicotine induced dopamine elevations in the nucleus accumbens shell in rats" British Journal of Pharmacology (2012) 165 2539-2548.
Zhou, "Design, Synthesis, Cytoselective Toxicity, Structure-Activity Relationships, and Pharmacophore of Thiazolidinone Derivatives Targeting Drug-Resistant Lung Cancer Cells" J. Med. Chem. 2008, 51, 1242-1251.

* cited by examiner

A ETI-T-174

B ETI-T-348

C ETI-T-209

Figure 3:
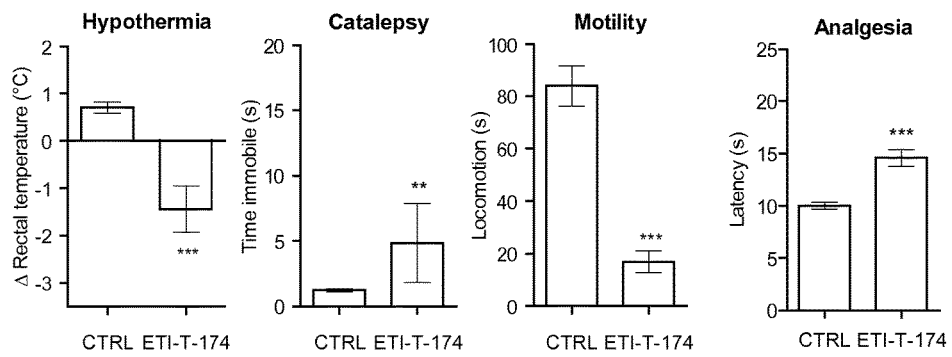
Figure 3:
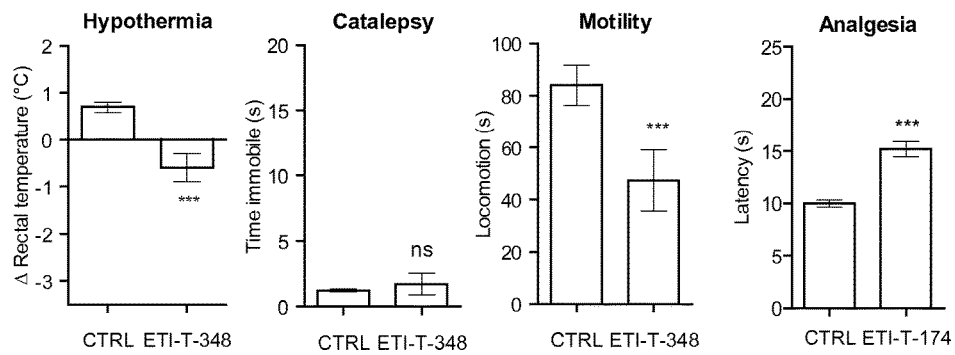
Figure 3:
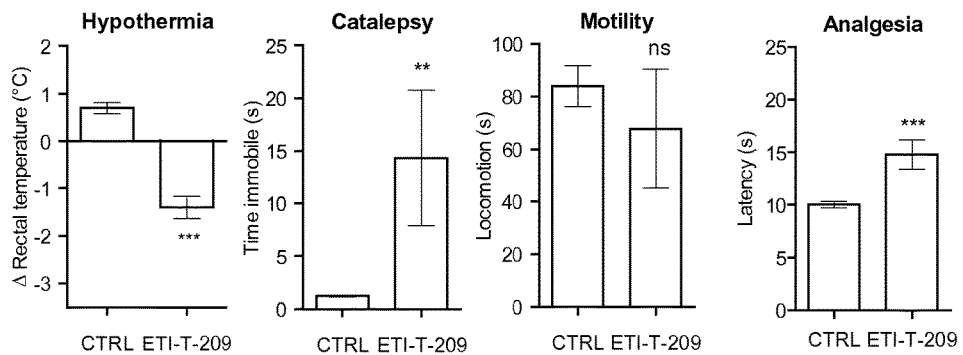

Fig. 3 (continuation)
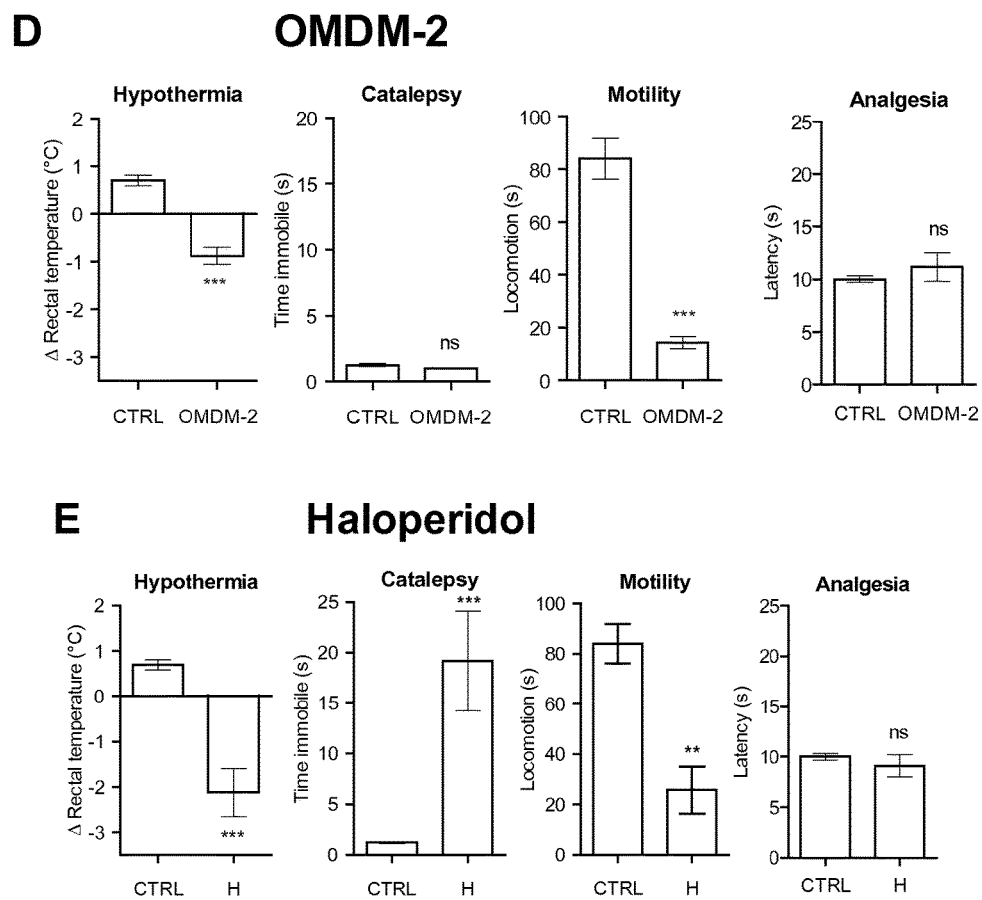

THIAZOLIDINONES AS CELLULAR ANANDAMIDE UPTAKE INHIBITORS AND THEIR USE IN THE TREATMENT OF PSYCHIATRIC OR NEUROLOGICAL DISORDERS AND INFLAMMATION, IN PARTICULAR NEUROINFLAMMATION

CROSS-REFERENCE TO RELATED APPLICATIONS

This is the U.S. National Stage of International Application No. PCT/EP2015/061914, filed May 28, 2015, which was published in English under PCT Article 21(2), and which in turn claims the benefit of European Patent Application numbers 14171022.8 filed on Jun. 3, 2014 and 14170448.6 filed on May 28, 2014.

FIELD OF THE INVENTION

The present invention relates to a class of thiazolidinone derivatives as cellular anandamide uptake inhibitors and their use in the treatment of psychiatric or neurological disorders and inflammation, in particular neuroinflammation.

BACKGROUND OF THE INVENTION

The endocannabinoid system (ECS) is a lipid signaling system comprising endocannabinoids (ECs), which are lipids derived from arachidonic acid, the G-protein-coupled cannabinoid receptors CB1 and CB2, as well as several other actual and potential physiological targets involved in the synthesis, transport and degradation of ECs. The major ECs are 2-arachidonoylglycerol (2-AG) and N-arachidonoyl ethanolamide (AEA; anandamide) which modulate synaptic transmission by retrograde signaling via CB1 receptors and exert potent immunomodulatory effects via both CB1 and CB2 receptors. The ECS has been implicated in physiological and pathophysiological conditions including inflammation, pain, psychiatric disorders and metabolic reprogramming. The ECS provides a primary on-demand protection system against acute excitotoxicity in the central nervous system (CNS) (Marsicano et al., 2003, Science, 302, 84-8.)

Therapeutic strategies within the ECS include the use of cannabinoid receptor agonists and antagonists, blockage of hydrolytic enzymes degrading ECs, such as fatty acid amide hydrolase (FAAH) and monoacylglycerol lipase (MAGL), as well as inhibition of EC cell membrane trafficking. Although so far no membrane protein for EC transport has been identified, several lines of evidence suggest a facilitated membrane transport involving both membrane and cytoplasmic targets (Chicca et al., 2012, J Biol Chem. 287, 36944-67; Fowler C J., 2013, FEBS J., 280:1895-904). The movement of AEA across the cell is affected by the concentration gradient enhanced by rapid intracellular hydrolysis of AEA catalyzed by FAAH. Therefore, FAAH plays a key role in AEA cellular uptake by generating an inward concentration gradient for AEA, which is the major driving force for its cellular uptake.

Using the commercially available AEA uptake inhibitors UCM707, OMDM-2 and LY2183240 evidence for bidirectional transport of both AEA and 2-AG across cell membranes, as well as a common mechanism of cellular membrane transport for all arachidonate-based ECs was recently provided (Chicca et al., 2012, J Biol Chem. 287, 36944-67). Since all of the available inhibitors are only moderately potent and show low selectivity towards AEA transport inhibition over FAAH inhibition or other cytoplasmic targets, investigations of the mechanisms of AEA and 2-AG cellular uptake are hampered by a lack of adequate tools. As indicated by a recent study (Nicolussi et al., Pharmacol Res., 2014, 80:52-65), the CNS pharmacology of inhibitors of endocannabinoid breakdown and inhibitors of endocannabinoid membrane transport is distinctly different and that inhibition of FAAH and AEA cellular uptake, respectively, can be independent from each other. Prior art has shown the use of Dodeca-2E,4E-diene amides as specific AEA cellular uptake inhibitors as anti-inflammatory agents in skin (WO 2010136221 A1). The potential therapeutic value of specific AEA cellular uptake inhibitors to treat CNS related diseases remains largely unknown. In a murine model of multiple sclerosis, the AEA cell membrane transport and FAAH inhibitor UCM707 showed beneficial effects by reducing microglial activation (Ortega-Gutierrez et al., 2005, FASEB J., 19, 1338-40). Using UCM707, it was shown that an increased AEA tone limits excitotoxicity in vitro and in a model of multiple sclerosis (Loria et al., 2010, Neurobiol Dis., 37, 166-76). The non-specific AEA cellular uptake and FAAH inhibitor AM404 was shown to reduce the rewarding effects of nicotine and nicotine-induced dopamine elevations in the nucleus accumbens shell in rats (Sherma et al., Br J Pharmacol., 2012, 165, 2539-48). The non-specific AEA cell membrane transport inhibitor VDM-11 was shown to modulate sleep and c-Fos expression in the rat brain (Murillo-Rodriguez et al., Neuroscience, 2008, 157, 1-11). The administration of AEA cell membrane transport inhibitors OMDM-2 or VDM-11 was shown to promote sleep and decreases extracellular levels of dopamine in rats (Murillo-Rodriguez et al., Physiol Behav. 2013, 109, 88-95). UCM707 was shown to behave as a symptom control agent in models of Huntington's disease and multiple sclerosis, but failed to delay/arrest the progression of different motor-related disorders (de Lago et al., Eur Neuropsychopharmacol., 2006, 16, 7-18). As shown by a study using UCM707 and AM404, AEA transport inhibitors may have potential in the treatment of painful diabetic neuropathy (Hasanein and Soltani, 2009, Clin Exp Pharmacol Physiol. 36, 1127-31). Targeting fatty acid binding protein (FABP) intracellular AEA carriers has recently been suggested to be a strategy to generate anti-inflammatory and anti-nociceptive drugs (Berger et al., 2012, PLoS One., 7(12):e50968.). However, the pharmacology between the inhibition of AEA cell membrane transport and the inhibition of cytoplasmic carriers is expected to be different, as exemplified by the fact that FABP5 inhibitors do apparently not show the same degree of cannabimimetic effects observed with the potent AEA cell membrane transport inhibitor guineensine (Kaczocha et al., PLoS One. 2014, 9(4):e94200; Nicolussi et al., 2014, Pharmacol Res., 80, 52-65).

Overall, there is a need for novel inhibitors of AEA cell membrane transport with superior specificity and potency to address CNS and inflammation related diseases involving aberrant endocannabinoid tone or in which AEA cellular uptake inhibition can target pathophysiological conditions. Given the fact that AEA and other endocannabinoids are involved in both synaptic processes via retrograde signaling and immunomodulatory processes, specific inhibitors of AEA cell membrane transport are expected to exert therapeutic effects in neuropsychiatric diseases involving neuroinflammation. When the degradation of AEA and other endocannabinoids is blocked, for example by covalent inhibition of FAAH, the resulting intracellular accumulation of AEA (Chicca et al., 2012, J Biol Chem., 287, 36944-67) is expected to potentially also have proinflammatory effects via oxygenation of AEA and possibly other endocannabinoids by cyclooxygenase-2 (discussed in Chicca et al, 2014, ACS Chem Biol, available on-line at pubs.acs.org/doi/abs/10.1021/cb500177c). Therefore, the inhibition of degradation of AEA and the inhibition of cell membrane transport are distinct pharmacological interventions. Moreover, specific inhibition of AEA cell membrane transport, unlike inhibition of FAAH or cytoplasmic carriers, is expected to differentially modulate the AEA tone without leading to activation of TRPV1 channels via intracellular AEA accumulation.

Our attention, therefore, is focused on the identification of a new class of molecules able to potently inhibit AEA cellular uptake. We show that these compounds trigger cannabimimetic behavioral effects and inhibit inflammation, in particular neuroinflammation.

The present invention relates to thiazolidinone derivatives and their use for the treatment of psychiatric or neurological disorders and inflammation, in particular neuroinflammation. The use of the compounds of the invention in a method for treatment of psychiatric or neurological disorders is related to attenuation of neuroinflammation and neuronal retrograde signaling mediated via AEA and other endocannabinoids. In example, such diseases include multiple sclerosis, epilepsy, Alzheimers disease, bipolar diseases, schizophrenia, sleeping disorders, and spinal cord injury (Ashton and Moore, Acta Psychiatr Scand. 2011, 124, 250-61.; Aso and Ferrer I, Front Pharmacol., 2014, 5, 37; Correa et al. Vitam Horm. 2009, 81, 207-30; Hofmann and Frazier, Exp Neurol. 2013, 244, 43-50; Pacher et al., Pharmacol Rev., 2006, 58, 389-462).

SUMMARY OF THE INVENTION

A first aspect of the invention relates to a compound characterized by a general formula 1 for use in the treatment of psychiatric or neurological disorders and inflammation, in particular neuroinflammation,

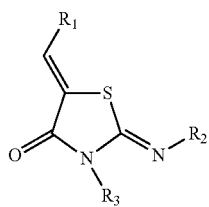

(formula 1)

wherein each of $R^1$, $R^2$ and $R^3$ are selected independently from each other from
  a substituted or unsubstituted alkyl, in particular a substituted or unsubstituted $C_1$-$C_8$ alkyl,
  a substituted or unsubstituted alkoxy, in particular a substituted or unsubstituted $C_1$-$C_8$ alkoxy,
  a substituted or unsubstituted alkenyl, in particular a substituted or unsubstituted $C_1$-$C_8$ alkenyl,
  a substituted or unsubstituted alkynyl, in particular a substituted or unsubstituted $C_1$-$C_8$ alkynyl,
  a substituted or unsubstituted cycloalkyl, in particular a substituted or unsubstituted $C_3$-$C_8$ cycloalkyl,
  a substituted or unsubstituted aryl, in particular a substituted or unsubstituted $C_6$-$C_{10}$ aryl,
  a substituted or unsubstituted heterocycle, in particular a substituted or unsubstituted $C_3$-$C_8$ heterocycle, or
  a substituted or unsubstituted heteroaryl, in particular a substituted or unsubstituted $C_5$-$C_{10}$ heteroaryl.

A second aspect of the invention relates to a compound characterized by a general formula 1,

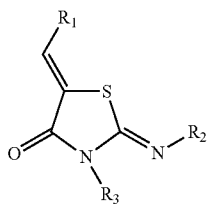

(formula 1)

wherein each of $R^1$, $R^2$ and $R^3$ are selected independently from each other from
  a substituted or unsubstituted alkyl, in particular a substituted or unsubstituted $C_1$-$C_8$ alkyl,
  a substituted or unsubstituted alkoxy, in particular a substituted or unsubstituted $C_1$-$C_8$ alkoxy,
  a substituted or unsubstituted alkenyl, in particular a substituted or unsubstituted $C_1$-$C_8$ alkenyl,
  a substituted or unsubstituted alkynyl, in particular a substituted or unsubstituted $C_1$-$C_8$ alkynyl,
  a substituted or unsubstituted cycloalkyl, in particular a substituted or unsubstituted $C_3$-$C_8$ cycloalkyl,
  a substituted or unsubstituted aryl, in particular a substituted or unsubstituted $C_6$-$C_{10}$ aryl,
  a substituted or unsubstituted heterocycle, in particular a substituted or unsubstituted $C_3$-$C_8$ heterocycle, or
  a substituted or unsubstituted heteroaryl, in particular a substituted or unsubstituted $C_5$-$C_{10}$ heteroaryl.

A third aspect of the invention relates to a pharmaceutical preparation for use in the treatment of psychiatric or neurological disorders and inflammation, in particular neuroinflammation comprising at least one compound according to the first or second aspect of the invention.

A fourth aspect of the invention relates to the compound of the first aspect of the invention for use as an endocannabinoid system modulator.

A fifth aspect of the invention relates to the compound of the first aspect of the invention for use as a AEA uptake Inhibitor.

The term "substituted" refers to the addition of a substituent group to a parent moiety.

"Substituent groups" can be protected or unprotected and can be added to one available site or to many available sites in a parent moiety. Substituent groups may also be further substituted with other substituent groups and may be attached directly or by a linking group such as an alkyl, an amide or hydrocarbyl group to a parent moiety. "Substituent groups" amenable herein include, without limitation, halogen, oxygen, nitrogen, sulphur, hydroxyl, alkyl, alkenyl, alkynyl, acyl, carboxyl, aliphatic groups, alicyclic groups, alkoxy, substituted oxy, aryl, aralkyl, amino, imino, amido fluorinated compounds etc.

As used herein the term "alkyl," refers to a saturated straight or branched hydrocarbon moiety containing up to 8, particularly up to 4 carbon atoms. Examples of alkyl groups include, without limitation, methyl, ethyl, propyl, butyl, isopropyl, n-hexyl, octyl, and the like. Alkyl groups typically include from 1 to about 8 carbon atoms ($C_1$-$C_8$ alkyl), particularly with from 1 to about 4 carbon atoms ($C_1$-$C_4$ alkyl).

As used herein the term "cycloalkyl" refers to an interconnected alkyl group forming a saturated or unsaturated ring or polyring structure containing 3 to 10, particularly 5 to 10 carbon atoms. Examples of cycloalkyl groups include, without limitation, cyclopropane, cyclopentane, cyclohexane, norbornane, decaline or adamantan (Tricyclo [3.3.1.1]decan), and the like. Cycloalkyl groups typically include from 5 to 10 carbon atoms ($C_5$-$C_{10}$ cycloalkyl).

Alkyl or cycloalkyl groups as used herein may optionally include further substituent groups. A substitution on the cycloalkyl group also encompasses an aryl, a heterocycle or a heteroaryl substituent, which can be connected to the cycloalkyl group via one atom or two atoms of the cycloalkyl group.

As used herein the term "alkenyl," refers to a straight or branched hydrocarbon chain moiety containing up to 8 carbon atoms and having at least one carbon-carbon double bond. Examples of alkenyl groups include, without limitation, ethenyl, propenyl, butenyl, 1-methyl-2-buten-1-yl, dienes such as 1,3-butadiene and the like. Alkenyl groups typically include from 2 to about 8 carbon atoms, more typically from 2 to about 4 carbon atoms. Alkenyl groups as used herein may optionally include further substituent groups.

As used herein the term "alkynyl," refers to a straight or branched hydrocarbon moiety containing up to 8 carbon atoms and having at least one carbon-carbon triple bond. Examples of alkynyl groups include, without limitation, ethynyl, 1-propynyl, 1-butynyl, and the like. Alkynyl groups typically include from 2 to about 8 carbon atoms, more typically from 2 to about 4 carbon atoms. Alkynyl groups as used herein may optionally include further substituent groups.

As used herein the term "alkoxy," refers to an oxygen alkyl moiety containing 1 to 8, particularly 1 to 4 carbon atoms comprising at least one oxygen moiety instead of a $CH_2$ moiety. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups. Furthermore, "alkoxy" groups include straight or branched ether groups (e. g. —$CH_2$—$CH_2$—O—$CH_3$) or polyether groups, which comprise several interconnected monomer alkoxy groups (e. g. —O—$CH_2$—$CH_2$—O—$CH_3$).

As used herein the term "heterocycle" refers to an interconnected alkyl group forming a saturated (or partially saturated) or unsaturated, in particular a saturated, ring or polyring structure containing 3 to 10, particularly 5 to 10 carbon atoms in which at least one carbon atom is replaced with an oxygen, a nitrogen or a sulphur atom forming a nonaromatic structure. Heterocyclic groups as used herein may optionally include further substituent groups. A substitution on the heterocyclic group also encompasses an aryl, a cycloalkyl or a heteroaryl substituent, which can be connected to the heterocyclic group via one atom or two atoms of the heterocyclic group (comparable to indole).

As used herein the term "aryl" refers to a hydrocarbon with alternating double and single bonds between the carbon atoms forming an aromatic ring structure, in particular a six ($C_6$ to ten ($C_{10}$) membered ring or polyring structure. The term "heteroaryl" refers to aromatic structures comprising a five to ten membered ring or polyring structure, comparable to aryl compounds, in which at least one member is an oxygen or a nitrogen or a sulphur atom. Due to simplicity reasons they are denominated $C_5$ to $C_{10}$ heteroaryl, wherein at least one carbon atom is replaced with an oxygen, a nitrogen or a sulphur atom forming an aromatic structure. For example a $C_5$ heteroaryl comprises a five membered ring structure with at least one carbon atom being replaced with an oxygen, a nitrogen or a sulphur atom. Aryl or hetero aryl groups as used herein may optionally include further substituent groups. A substitution on the hetero aryl group also encompasses an aryl, a cycloalkyl or a heterocycle substituent, which can be connected to the hetero aryl via one atom or two atoms of the hetero aryl group (comparable to indole). The same applies to an aryl group.

As used herein "*" indicates a center of a E- or Z-isomer structure, which is located on the atom below the asterisk *.

DETAILED DESCRIPTION OF THE INVENTION

A first aspect of the invention relates to compounds of a general formula 1 for use in the treatment of psychiatric or neurological disorders and inflammation, in particular neuroinflammation,

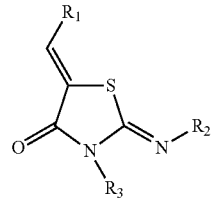

(formula 1)

wherein each of $R^1$, $R^2$ and $R^3$ are selected independently from each other from
a substituted or unsubstituted alkyl, in particular a substituted or unsubstituted $C_1$-$C_8$ alkyl,
a substituted or unsubstituted alkoxy, in particular a substituted or unsubstituted $C_1$-$C_8$ alkoxy,
a substituted or unsubstituted alkenyl, in particular a substituted or unsubstituted $C_1$-$C_8$ alkenyl,
a substituted or unsubstituted alkynyl, in particular a substituted or unsubstituted $C_1$-$C_8$ alkynyl,
a substituted or unsubstituted cycloalkyl, in particular a substituted or unsubstituted $C_3$-$C_8$ cycloalkyl,
a substituted or unsubstituted aryl, in particular a substituted or unsubstituted $C_6$-$C_{10}$ aryl,
a substituted or unsubstituted heterocycle, in particular a substituted or unsubstituted $C_3$-$C_8$ heterocycle, or
a substituted or unsubstituted heteroaryl, in particular a substituted or unsubstituted $C_5$-$C_{10}$ heteroaryl.

In some embodiments $R^2$ is selected from
a substituted or unsubstituted alkyl, in particular a substituted or unsubstituted $C_1$-$C_8$ alkyl,
a substituted or unsubstituted alkoxy, in particular a substituted or unsubstituted $C_1$-$C_8$ alkoxy,
a substituted or unsubstituted alkenyl, in particular a substituted or unsubstituted $C_1$-$C_8$ alkenyl,
a substituted or unsubstituted alkynyl, in particular a substituted or unsubstituted $C_1$-$C_8$ alkynyl,
a substituted or unsubstituted cycloalkyl, in particular a substituted or unsubstituted $C_3$-$C_8$ cycloalkyl,
a substituted or unsubstituted aryl, in particular a substituted or unsubstituted $C_6$-$C_{10}$ aryl,
a substituted or unsubstituted heterocycle, in particular a substituted or unsubstituted $C_3$-$C_8$ heterocycle, or
a substituted or unsubstituted heteroaryl, in particular a substituted or unsubstituted $C_5$-$C_{10}$ heteroaryl.

In some embodiments $R^2$ is selected from
a substituted or unsubstituted alkyl, in particular a substituted or unsubstituted $C_1$-$C_8$ alkyl,
a substituted or unsubstituted alkoxy, in particular a substituted or unsubstituted $C_1$-$C_8$ alkoxy,
a substituted or unsubstituted aryl, in particular a substituted or unsubstituted $C_6$-$C_{10}$ aryl, or
a substituted or unsubstituted heterocycle, in particular a substituted or unsubstituted $C_3$-$C_8$ heterocycle.

In some embodiments $R^2$ is selected from
a substituted or unsubstituted aryl, in particular a substituted or unsubstituted $C_6$-$C_{10}$ aryl.

In some embodiments $R^3$ is selected from
a substituted or unsubstituted alkyl, in particular a substituted or unsubstituted $C_1$-$C_8$ alkyl,
a substituted or unsubstituted alkoxy, in particular a substituted or unsubstituted $C_1$-$C_8$ alkoxy,
a substituted or unsubstituted alkenyl, in particular a substituted or unsubstituted $C_1$-$C_8$ alkenyl,
a substituted or unsubstituted alkynyl, in particular a substituted or unsubstituted $C_1$-$C_8$ alkynyl,
a substituted or unsubstituted cycloalkyl, in particular a substituted or unsubstituted $C_3$-$C_8$ cycloalkyl,
a substituted or unsubstituted aryl, in particular a substituted or unsubstituted $C_6$-$C_{10}$ aryl,
a substituted or unsubstituted heterocycle, in particular a substituted or unsubstituted $C_3$-$C_8$ heterocycle, or
a substituted or unsubstituted heteroaryl, in particular a substituted or unsubstituted $C_5$-$C_{10}$ heteroaryl.

In some embodiments $R^3$ is selected from
a substituted or unsubstituted alkyl, in particular a substituted or unsubstituted $C_1$-$C_8$ alkyl,
a substituted or unsubstituted alkoxy, in particular a substituted or unsubstituted $C_1$-$C_8$ alkoxy,
a substituted or unsubstituted aryl, in particular a substituted or unsubstituted $C_6$-$C_{10}$ aryl, or
a substituted or unsubstituted heterocycle, in particular a substituted or unsubstituted $C_3$-$C_8$ heterocycle.

In some embodiments $R^3$ is selected from
a substituted or unsubstituted aryl, in particular a substituted or unsubstituted $C_6$-$C_{10}$ aryl.

In some embodiments $R^1$ is selected from
a substituted or unsubstituted aryl, in particular a substituted or unsubstituted $C_6$-$C_{10}$ aryl.

In some embodiments $R^1$ comprises the general formula 2

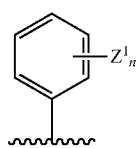

(formula 2)

with n of $Z^1_n$ being 0, 1, 2, 3, 4 or 5, and each $Z^1$ independently from any other $Z^1$ being selected from F, Cl, Br, I, —$R^a$, —$OR^a$ or —$NR^a_2$, with each $R^a$ being selected independently from each other from H, a substituted or unsubstituted $C_1$-$C_8$ alkyl, a substituted or unsubstituted $C_2$-$C_8$ alkenyl or a substituted or unsubstituted $C_2$-$C_8$ alkynyl.

In some embodiments $R^1$ comprises the general formula 2 with n of $Z^1_n$ being 0, 1, 2, 3, 4 or 5 and each $Z^1$ independently from any other $Z^1$ being selected from F, Cl, Br, I, —$R^a$, —$OR^a$ or —$NR^a_2$, with each $R^a$ being selected independently from each other from H, a substituted or unsubstituted $C_1$-$C_4$ alkyl, a substituted or unsubstituted $C_2$-$C_4$ alkenyl or a substituted or unsubstituted $C_2$-$C_4$ alkynyl.

In some embodiments $R^1$ comprises the general formula 2 with n of $Z^1_n$ being 1, 2 or 3, and each $Z^1$ independently from any other $Z^1$ being selected from F, Cl, Br, I, —$R^a$, —$OR^a$ or —$NR^a_2$, with each $R^a$ being selected independently from each other form H, a substituted or unsubstituted $C_1$-$C_8$ alkyl, a substituted or unsubstituted $C_2$-$C_8$ alkenyl, a substituted or unsubstituted $C_2$-$C_8$ alkynyl.

In some embodiments $R^1$ comprises the general formula 2 with n of $Z^1_n$ being 1, 2 or 3, and each $Z^1$ independently from any other $Z^1$ being selected from F, Cl, Br, I, —$R^a$, —$OR^a$ or —$NR^a_2$ with each $R^a$ being selected independently from each other from H, a substituted or unsubstituted $C_1$-$C_4$ alkyl, a substituted or unsubstituted $C_2$-$C_4$ alkenyl, a substituted or unsubstituted $C_2$-$C_4$ alkynyl.

In some embodiments $R^1$ comprises the general formula 2 with n of $Z^1_n$ being 1, 2 or 3, and each $Z^1$ independently from any other $Z^1$ being selected from —$OR^a$ with $R^a$ being selected from H, a substituted or unsubstituted $C_1$-$C_8$ alkyl, a substituted or unsubstituted $C_2$-$C_8$ alkenyl, a substituted or unsubstituted $C_2$-$C_8$ alkynyl.

In some embodiments $R^1$ comprises the general formula 2 with n of $Z^1_n$ being 1, 2 or 3, and each $Z^1$ independently from any other $Z^1$ being selected from —$OR^a$ with $R^a$ being selected from H, a substituted or unsubstituted $C_1$-$C_4$ alkyl, a substituted or unsubstituted $C_2$-$C_4$ alkenyl, a substituted or unsubstituted $C_2$-$C_4$ alkynyl.

In some embodiments $R^1$ comprises the general formula 3

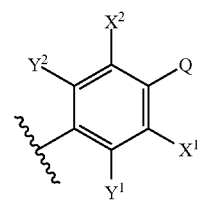

(formula 3)

with Q being F, Cl, Br, I, —$R^b$, —$OR^b$ or —$NR^b_2$, and with each $R^b$ being selected independently from each other from
H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, and with $X^1$ and $X^2$ being selected independently from each other from F, Cl, Br, I, —$R^c$, —$OR^c$ or —$NR^c_2$, and with each $R^c$ being selected independently from each other from
H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, and with $Y^1$ and $Y^2$ being selected independently from each other from F, Cl, Br, I, —$R^d$ or —$OR^d$ or —$NR^d_2$, in particular from —$OR^d$, and with each $R^d$ being selected independently from each other from
H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl.

In some embodiments $R^1$ comprises the general formula 3 with
Q being —$OR^b$ with $R^b$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, or a substituted or unsubstituted $C_2$-$C_8$ alkenyl, in particular $C_2$-$C_4$ alkenyl, in particular from a substituted or unsubstituted $C_1$-$C_8$ alkyl, in particular $C_1$-$C_4$ alkyl, or a substituted or unsubstituted $C_2$-$C_8$ alkynyl, in particular $C_2$-$C_4$ alkynyl,
or
Q being —$NR^b_2$ with each $R^b$ being selected independently from each other H, or a substituted or unsubstituted $C_1$-$C_8$ alkyl, in particular $C_1$-$C_4$ alkyl.

In some embodiments $R^1$ comprises the general formula 3 with Q being —$OR^b$, with $R^b$ being selected from H, a substituted or unsubstituted $C_1$-$C_8$ alkyl, in particular $C_1$-$C_4$ alkyl, or a substituted or unsubstituted $C_2$-$C_8$ alkynyl, in particular $C_2$-$C_4$ alkynyl.

In some embodiments $R^1$ comprises the general formula 3 with Q being —$OR^b$, with $R^b$ being selected from H, a substituted or unsubstituted $C_1$-$C_8$ alkyl, in particular $C_1$-$C_4$ alkyl.

In some embodiments $R^1$ comprises the general formula 3 with Q being selected from —OH, —$OCH_3$, —$OCH_2CH_3$, —$O(CH_2)_2CH_3$, —$O(CH_2)CCH$, in particular Q is selected from —OH or —$OCH_3$, more particularly Q is OH.

In some embodiments $R^1$ comprises the general formula 3 with $X^1$ and $X^2$ being selected independently from each other from
F, Cl, Br, I or
—$R^c$, with $R^c$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or
—$OR^c$, with $R^c$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments $R^1$ comprises the general formula 3 with $X^1$ and $X^2$ being selected independently from each other from —$OR^c$, with $R^c$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments $R^1$ comprises the general formula 3 with $X^1$ and $X^2$ being selected independently from each other from H, —$OCH_3$ or —$OCH_2CH_3$.

In some embodiments $R^1$ comprises the general formula 3 with $X^1$ and $X^2$ being selected independently from each other from H, —$OCH_3$ or —$OCH_2CH_3$, wherein Q has the same meaning as defined previously.

In some embodiments $R^1$ comprises the general formula 3 with $Y^1$ and $Y^2$ are selected independently from each other from
F, Cl, Br, I, or
—$R^d$, with $R^d$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or
—$OR^d$, with $R^d$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments $R^1$ comprises the general formula 3 with $Y^1$ and $Y^2$ being selected independently from each other from —$OR^c$, with $R^c$ being selected from H, or a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments $R^1$ comprises the general formula 3 with $Y^1$ and $Y^2$ being selected independently from each other from H or —$OCH_3$.

In some embodiments $R^1$ comprises the general formula 3 with $Y^1$ and $Y^2$ being H.

In some embodiments $R^1$ comprises the general formula 3 with $Y^1$ and $Y^2$ being H, wherein Q and/or $Y^1$ and $Y^2$ having the same meaning as defined previously.

In some embodiments $R^1$ is selected from moiety 1 to 23 as depicted below:

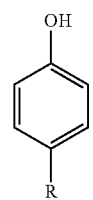

(1)

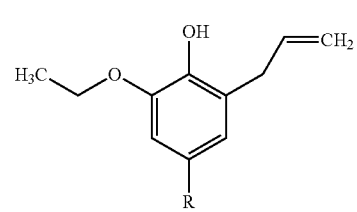

(2)

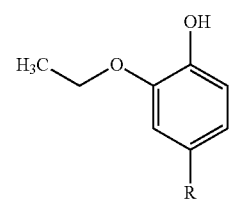

(3)

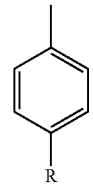

(4)

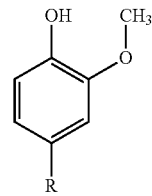

(5)

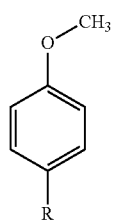 (6)
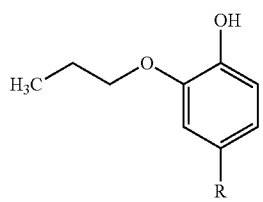 (7)
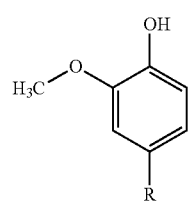 (8)
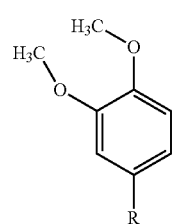 (9)
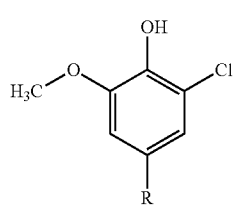 (10)
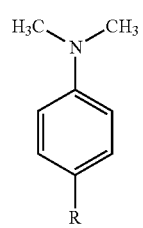 (11)
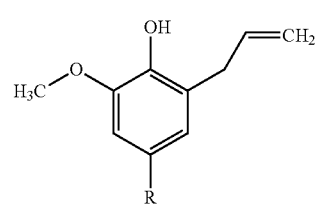 (12)
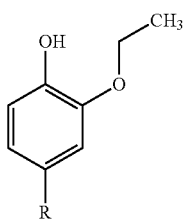 (13)
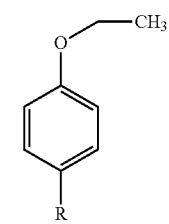 (14)
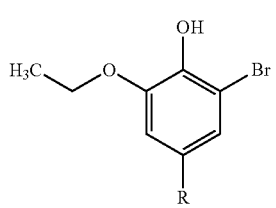 (15)
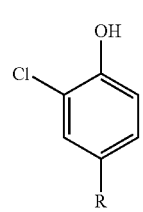 (16)
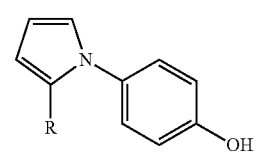 (17)
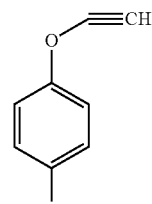 (18)
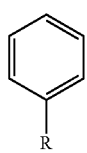 (19)
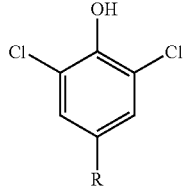 (20)

13

-continued

(21)
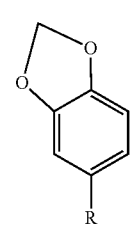

(22)
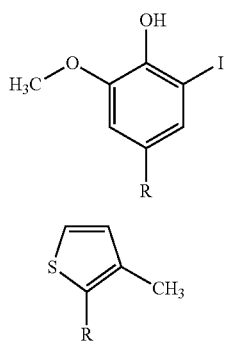

(23)
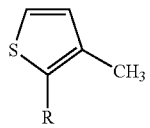

with R indicating in this embodiment the connection to the parent moiety of the compound of the formula 1.

In some embodiments $R^1$ is selected from the moiety 1 to 16, 18 to 20 or 22 as depicted above.

In some embodiments $R^1$ is selected from the moiety 1, 4, 6, 11, 14, 18 or 19 as depicted above.

In some embodiments $R^1$ is selected from the moiety 1, 6, 14 or 18 as depicted above.

In some embodiments $R^1$ is selected from the moiety 1 or 6 as depicted above.

In some embodiments according to a first sub aspect of the first aspect of the invention, $R^1$ is selected from
- a substituted or unsubstituted alkyl, in particular a substituted or unsubstituted $C_1$-$C_8$ alkyl,
- a substituted or unsubstituted alkoxy, in particular a substituted or unsubstituted $C_1$-$C_8$ alkoxy,
- a substituted or unsubstituted alkenyl, in particular a substituted or unsubstituted $C_1$-$C_8$ alkenyl,
- a substituted or unsubstituted alkynyl, in particular a substituted or unsubstituted $C_1$-$C_8$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, and $R^2$ is selected from
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, and $R^3$ is selected from
- a substituted or unsubstituted cycloalkyl, in particular a substituted or unsubstituted $C_3$-$C_{10}$ cycloalkyl, in particular cyclohexane.

14

In some embodiments of the first sub aspect of the invention, $R^1$ is selected from a substituted or unsubstituted aryl, in particular a substituted or unsubstituted $C_6$-$C_{10}$ aryl.

In some embodiments of the first sub aspect of the invention, $R^1$ comprises the general formula 2

(formula 2)
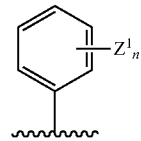

with n of $Z^1_n$ being 0, 1, 2, 3, 4 or 5, in particular n of $Z^1_n$ being 1, 2 or 3, and with each $Z^1$ independently from any other $Z^1$ being selected from
—F, —Cl, —Br, —I, —$R^a$, —$OR^a$ or —$NR^a_2$, in particular form —$OR^a$,
with each $R^a$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl.

In some embodiments of the first sub aspect of the invention, $R^1$ comprises the general formula 3

(formula 3)
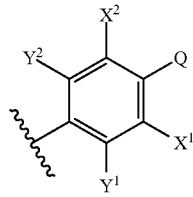

with Q being F, Cl, Br, I, —$R^b$, —$OR^b$ or —$NR^b_2$, and
with each $R^b$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, and
with $X^1$ and $X^2$ being selected independently from each other from F, Cl, Br, I, —$R^c$ or —$OR^c$ or —$NR^c_2$, and
with each $R^c$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, and
with $Y^1$ and $Y^2$ being selected independently from each other from F, Cl, Br, I, —$R^d$ or —$OR^d$ or —$NR^d_2$, and
with each $R^d$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl.

In some embodiments of the first sub aspect of the invention, $R^1$ comprises the general formula 3 with
Q being —$OR^b$ with $R^b$ being selected from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or Q being —$NR^b{}_2$ with each $R^b$ being selected independently from each other H, or a substituted or unsubstituted $C_1$-$C_8$ alkyl, in particular $C_1$-$C_4$ alkyl.

In some embodiments of the first sub aspect of the invention, $R^1$ comprises the general formula 3 with Q being —$OR^b$, with $R^b$ being selected from H, a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, in particular from H or a substituted or unsubstituted $C_1$-$C_8$ alkyl, in particular $C_1$-$C_4$ alkyl.

In some embodiments of the first sub aspect of the invention, $R^1$ comprises the general formula 3, with Q being —$OR^b$, with $R^b$ being selected from —OH, —$OCH_3$, —$OCH_2CH_3$, —$O(CH_2)_2CH_3$, —$O(CH_2)CCH$, in particular $R^b$ is selected from —OH or —$OCH_3$, more particularly $R^b$ is OH.

In some embodiments of the first sub aspect of the invention, $R^1$ comprises the general formula 3 with $X^1$ and $X^2$ being selected independently from each other from
F, Cl, Br, I or
—$R^c$, with $R^c$ being selected from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or
—$OR^c$, with $R^c$ being selected from H, a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments of the first sub aspect of the invention, $R^1$ comprises the general formula 3 with $X^1$ and $X^2$ being selected independently from each other from —$OR^c$, with $R^c$ being selected from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, in particular with $X^1$ and $X^2$ being selected independently from each other from H, —$OCH_3$ or —$OCH_2CH_3$.

In some embodiments of the first sub aspect of the invention, $R^1$ comprises the general formula 3 with $Y^1$ and $Y^2$ are selected independently from each other from
F, Cl, Br, I, or
—$R^d$, with $R^d$ being selected from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or
—$OR^d$, with $R^d$ being selected from H, a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments of the first sub aspect of the invention, $R^1$ comprises the general formula 3 with $Y^1$ and $Y^2$ being selected independently from each other from —$OR^c$, with $R^c$ being selected from H, a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, in particular with $Y^1$ and $Y^2$ being selected independently from each other from H or —$OCH_3$, more particularly H.

Specific embodiments discussed before the first sub aspect of the invention may be combined with the first sub aspect.

In some embodiments according to a second sub aspect of the invention, each of $R^2$ and $R^3$ are selected independently from each other from
a substituted or unsubstituted alkyl, in particular a substituted or unsubstituted $C_1$-$C_8$ alkyl,
a substituted or unsubstituted alkoxy, in particular a substituted or unsubstituted $C_1$-$C_8$ alkoxy,
a substituted or unsubstituted alkenyl, in particular a substituted or unsubstituted $C_1$-$C_8$ alkenyl,
a substituted or unsubstituted alkynyl, in particular a substituted or unsubstituted $C_1$-$C_8$ alkynyl,
a substituted or unsubstituted cycloalkyl, in particular a substituted or unsubstituted $C_3$-$C_{10}$ cycloalkyl,
a substituted or unsubstituted aryl, in particular a substituted or unsubstituted $C_6$-$C_{10}$ aryl,
a substituted or unsubstituted saturated heterocycle, in particular a substituted or unsubstituted $C_3$-$C_{10}$ heterocycle, or
a substituted or unsubstituted heteroaryl, in particular a substituted or unsubstituted $C_5$-$C_{10}$ heteroaryl, wherein $R^1$ comprises the general formula 3

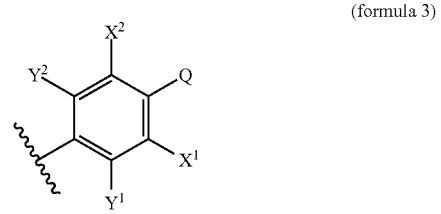

(formula 3)

with Q being
F, Cl, Br, I, or
—$R^b$, with —$R^b$ being H, or
—$R^b$, with —$R^b$ being a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or
—$OR^b$, with —$OR^b$ being H and
with at least one of $X^1$ or $X^2$ being selected from
—$R^c$ with each $R^c$ being selected independently from each other from a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, in particular a substituted or unsubstituted $C_2$-$C_8$ alkenyl, in particular $C_2$-$C_4$ alkenyl, or
—$OR^c$ with each $R^c$ being selected independently from each other from a unsubstituted $C_3$-$C_4$ alkyl, in particular a $C_3$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, in particular a substituted or unsubstituted $C_2$-$C_8$ alkenyl, in particular $C_2$-$C_4$ alkenyl, or
F, Br, I, wherein
the other one of $X^1$ or $X^2$ being selected from
F, Cl, Br, I, —$R^c$ or —$OR^c$ or —$NR^c{}_2$, and with each $R^c$ being selected independently from each other from
H,
a substituted or unsubstituted $C_1$-$C_8$ alkyl, in particular $C_1$-$C_4$ alkyl,
a substituted or unsubstituted $C_2$-$C_8$ alkenyl, in particular $C_2$-$C_4$ alkenyl, or
a substituted or unsubstituted $C_2$-$C_8$ alkynyl, in particular $C_2$-$C_4$ alkynyl, and with $Y^1$ and $Y^2$ being selected independently from each other from F, Cl, Br, I, —$R^d$ or —$OR^d$ or —$NR^d_2$, and with each $R^d$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or with at least one of $X^1$ or $X^2$ being selected from F, Cl, Br, I, and the other one of $X^1$ or $X^2$ being H or F, Cl, Br, I, and with $Y^1$ and $Y^2$ being selected independently from each other from F, Cl, Br, I, —$R^d$ or —$OR^d$ or —$NR^d_2$, and with each $R^d$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl.

In some embodiments of the second sub aspect of the invention, $R^1$ comprises the general formula 3 with $Y^1$ and $Y^2$ are selected independently from each other from F, Cl, Br, I, or —$R^d$, with $R^d$ being selected from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or —$OR^d$, with $R^d$ being selected from H, a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl.

In some embodiments of the second sub aspect of the invention, $R^1$ comprises the general formula 3 with $Y^1$ and $Y^2$ being selected independently from each other from —$OR^c$, with $R^c$ being selected from H, a substituted or unsubstituted $C_1$-$C_8$ alkyl, in particular $C_1$-$C_4$ alkyl, or a substituted or unsubstituted $C_2$-$C_8$ alkenyl, in particular $C_2$-$C_4$ alkenyl, in particular with $Y^1$ and $Y^2$ being selected independently from each other from H or —$OCH_3$, more particularly H.

Specific embodiments discussed before the first sub aspect of the invention may be combined with the second sub aspect.

In some embodiments of a third sub aspect of the invention, each of $R^1$, $R^2$ and $R^3$ are selected independently from each other from a substituted or unsubstituted cycloalkyl, in particular a substituted or unsubstituted $C_3$-$C_{10}$ cycloalkyl, a substituted or unsubstituted aryl, in particular a substituted or unsubstituted $C_6$-$C_{10}$ aryl, a substituted or unsubstituted saturated heterocycle, in particular a substituted or unsubstituted $C_3$-$C_{10}$ heterocycle, or a substituted or unsubstituted heteroaryl, in particular a substituted or unsubstituted $C_5$-$C_{10}$ heteroaryl.

In some embodiments of the third sub aspect of the invention, $R^1$ is selected from a substituted or unsubstituted aryl, in particular a substituted or unsubstituted $C_6$-$C_{10}$ aryl.

In some embodiments of the third sub aspect of the invention, $R^1$ comprises the general formula 2

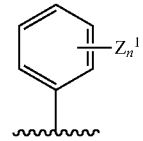

(formula 2)

with n of $Z^1_n$ being 0, 1, 2, 3, 4 or 5, in particular n of $Z^1_n$ being 1, 2 or 3, and with each $Z^1$ independently from any other $Z^1$ being selected from —F, —Cl, —Br, —I, —$R^a$, —$OR^a$ or —$NR^a_2$, in particular form —$OR^a$, with each $R^a$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl.

In some embodiments of the third sub aspect of the invention, $R^1$ comprises the general formula 3

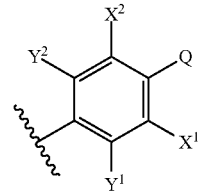

(formula 3)

with Q being F, Cl, Br, I, —$R^b$, —$OR^b$ or —$NR^b_2$, and with each $R^b$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, and with $X^1$ and $X^2$ being selected independently from each other from F, Cl, Br, I, —$R^c$ or —$OR^c$ or —$NR^c_2$, and with each $R^c$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, and with $Y^1$ and $Y^2$ being selected independently from each other from F, Cl, Br, I, —$R^d$ or —$OR^d$ or —$NR^d_2$, and with each $R^d$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl.

In some embodiments of the third sub aspect of the invention, $R^1$ comprises the general formula 3 with Q being —$OR^b$ with $R^b$ being selected from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, or Q being —$NR^b_2$ with each $R^b$ being selected independently from each other H, or a substituted or unsubstituted $C_1$-$C_8$ alkyl, in particular $C_1$-$C_4$ alkyl.

In some embodiments of the third sub aspect of the invention, $R^1$ comprises the general formula 3 with Q being —OR$^b$, with R$^b$ being selected from H, a substituted or unsubstituted C$_1$-C$_8$ alkyl, in particular C$_1$-C$_4$ alkyl, or a substituted or unsubstituted C$_2$-C$_8$ alkenyl, in particular C$_2$-C$_4$ alkenyl, in particular from H or a substituted or unsubstituted C$_1$-C$_8$ alkyl, in particular C$_1$-C$_4$ alkyl.

In some embodiments of the third sub aspect of the invention, R$^1$ comprises the general formula 3, with Q being —OR$^b$, with R$^b$ being selected from —OH, —OCH$_3$, —OCH$_2$CH$_3$, —O(CH$_2$)$_2$CH$_3$, —O(CH$_2$)CCH, in particular R$^b$ is selected from —OH or —OCH$_3$, more particularly R$^b$ is OH In some embodiments of the third sub aspect of the invention, R$^1$ comprises the general formula 3 with X$^1$ and X$^2$ being selected independently from each other from
F, Cl, Br, I or
—R$^c$, with R$^c$ being selected from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, or
—OR$^c$, with R$^c$ being selected from H, a substituted or unsubstituted C$_1$-C$_8$ alkyl, in particular C$_1$-C$_4$ alkyl, or a substituted or unsubstituted C$_2$-C$_8$ alkenyl, in particular C$_2$-C$_4$ alkenyl In some embodiments of the third sub aspect of the invention, R$^1$ comprises the general formula 3 with X$^1$ and X$^2$ being selected independently from each other from —OR$^c$, with R$^c$ being selected from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, in particular with X$^1$ and X$^2$ being selected independently from each other from H, —OCH$_3$ or —OCH$_2$CH$_3$ In some embodiments of the third sub aspect of the invention, R$^1$ comprises the general formula 3

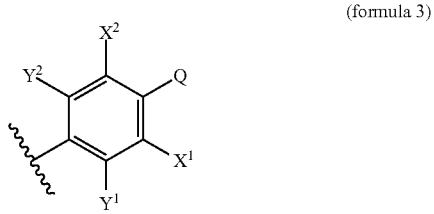

(formula 3)

with Q being
F, Cl, Br, I, or
R$^b$, with R$^b$ being H, or
R$^{b'}$ with R$^b$ being a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, or
—OR$^b$, with —OR$^b$ being H, and
with at least one of X$^1$ or X$^2$ being selected from
—R$^c$ with each R$^c$ being selected independently from each other from a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, in particular a substituted or unsubstituted C$_2$-C$_8$ alkenyl, in particular C$_2$-C$_4$ alkenyl, or
—OR$^c$ with each R$^c$ being selected independently from each other from a unsubstituted C$_3$-C$_4$ alkyl, in particular a C$_3$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, in particular a substituted or unsubstituted C$_2$-C$_8$ alkenyl, in particular C$_2$-C$_4$ alkenyl, or
F, Br, I, wherein
the other one of X$^1$ or X$^2$ being selected from
F, Cl, Br, I, —R$^c$ or —OR$^c$ or —NR$^c_2$, and with each R$^c$ being selected independently from each other from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, and
with Y$^1$ and Y$^2$ being selected independently from each other from
F, Cl, Br, I, —R$^d$ or —OR$^d$ or —NR$^d_2$, and with each R$^d$ being selected independently from each other from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, or with at least one of X$^1$ or X$^2$ being selected from F, Cl, Br, I, and the other one of X$^1$ or X$^2$ being H or F, Cl, Br, I, and with Y$^1$ and Y$^2$ being selected independently from each other from
F, Cl, Br, I, —R$^d$ or —OR$^d$ or —NR$^d_2$, and with each R$^d$ being selected independently from each other from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl.

In some embodiments of the third sub aspect of the invention, R$^1$ comprises the general formula 3 with Y$^1$ and Y$^2$ are selected independently from each other from
F, Cl, Br, I, or
—R$^d$, with R$^d$ being selected from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, or
—OR$^d$, with R$^d$ being selected from H, a substituted or unsubstituted C$_1$-C$_8$ alkyl, in particular C$_1$-C$_4$ alkyl, or a substituted or unsubstituted C$_2$-C$_8$ alkenyl, in particular C$_2$-C$_4$ alkenyl.

In some embodiments of the third sub aspect of the invention, R$^1$ comprises the general formula 3 with Y$^1$ and Y$^2$ being selected independently from each other from —OR$^c$, with R$^c$ being selected from H, a substituted or unsubstituted C$_1$-C$_8$ alkyl, in particular C$_1$-C$_4$ alkyl, or a substituted or unsubstituted C$_2$-C$_8$ alkenyl, in particular C$_2$-C$_4$ alkenyl, in particular with Y$^1$ and Y$^2$ being selected independently from each other from H or —OCH$_3$, more particularly H.

Specific embodiments discussed before the first sub aspect of the invention may be combined with the third sub aspect.

In some embodiments the compound of the invention comprises a (2Z,5Z), (2Z,5E), (2E,5Z) or (2E,5E) isomer form, in particular a (2Z,5Z) or (2Z,5E), more particularly a (2Z,5Z) isomer form, characterized by formula 1a

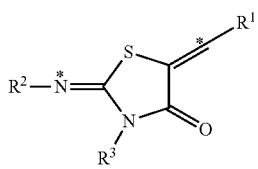

(formula 1a)

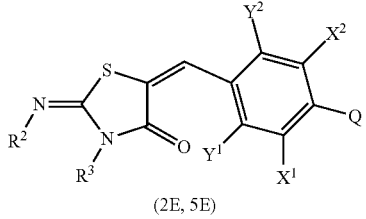

(formula 4d)
(2E, 5E)

with the isomer center being indicated by the asterix (*), with $R^1$, $R^2$ and $R^3$ having the same meaning as defined previously, wherein the compound of the invention comprises the before mentioned isomers in an essentially pure form.

As used herein the term "essentially pure" refers to a purity of >90%, in particular of >95%.

In some embodiments the compound of the invention comprises a mixture of the (2Z,5Z), (2Z,5E), (2E,5Z) or (2E,5E) isomer forms, in particular a mixture of (2Z,5Z) and (2Z,5E). characterized by formula 1a as depicted above.

In some embodiments the compound of the invention comprises a (2Z,5Z), (2Z,5E), (2E,5Z) or (2E,5E) isomer form, in particular a (2Z,5Z) or (2Z,5E), more particularly a (2Z,5Z) isomer form, characterized by the general formulas 4a, 4b, 4c or 4d,

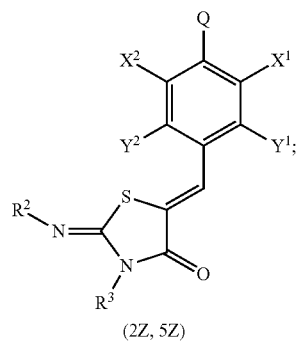

(formula 4a)

(2Z, 5Z)

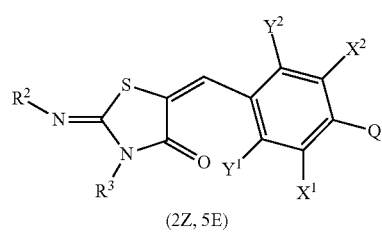

(formula 4b)

(2Z, 5E)

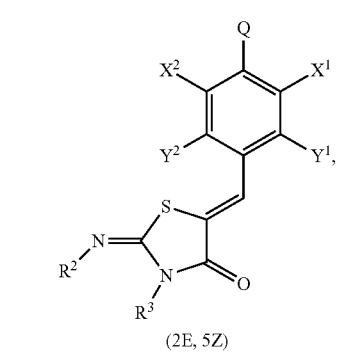

(formula 4c)

(2E, 5Z)

in particular by the general formulas 4a or 4b, more particularly by the formula 4a,
with $R^2$ and $R^3$ having the same meaning as defined previously, and $R^1$ comprises the general formula 3, with Q, $X^1$, $X^2$, $Y^1$ and $Y^2$ having the same meaning as defined previously,
wherein the compound of the invention comprises the before mentioned isomers in an essentially pure form.

In some embodiments the compound of the invention comprises a mixture of (2Z,5Z), (2Z,5E), (2E,5Z) or (2E,5E) isomer forms, in particular a mixture of (2Z,5Z) and (2Z, 5E), characterized by the general formulas 4a, 4b, 4c or 4d, in particular by the general formulas 4a or 4b, with $R^2$ and $R^3$ having the same meaning as defined previously, and $R^1$ comprises the general formula 3, with Q, $X^1$, $X^2$, $Y^1$ and $Y^2$ having the same meaning as defined previously.

A second aspect of the invention relates to a compound characterized by the formula 1, wherein preferred embodiments are discussed and defined in the first aspect of the invention. Any embodiment defined in the first aspect of the invention may be used in the second aspect of the invention.

A third aspect of the invention relates to a pharmaceutical preparation for use in the treatment of psychiatric or neurological disorders and inflammation, in particular neuroinflammation, comprising at least one compound according to the first or second aspect of the invention.

A fourth aspect of the invention relates to the compound of the first aspect, particularly the first, second and third sub aspect, of the invention for use as an endocannabinoid system modulator.

A fifth aspect of the invention relates to the compound of the first aspect, particularly the first, second and third sub aspect, of the invention for use as an AEA uptake Inhibitor.

The compounds of the invention may also be used as an analgesic. Reference is made to the figures and experimental section.

Figure 2:
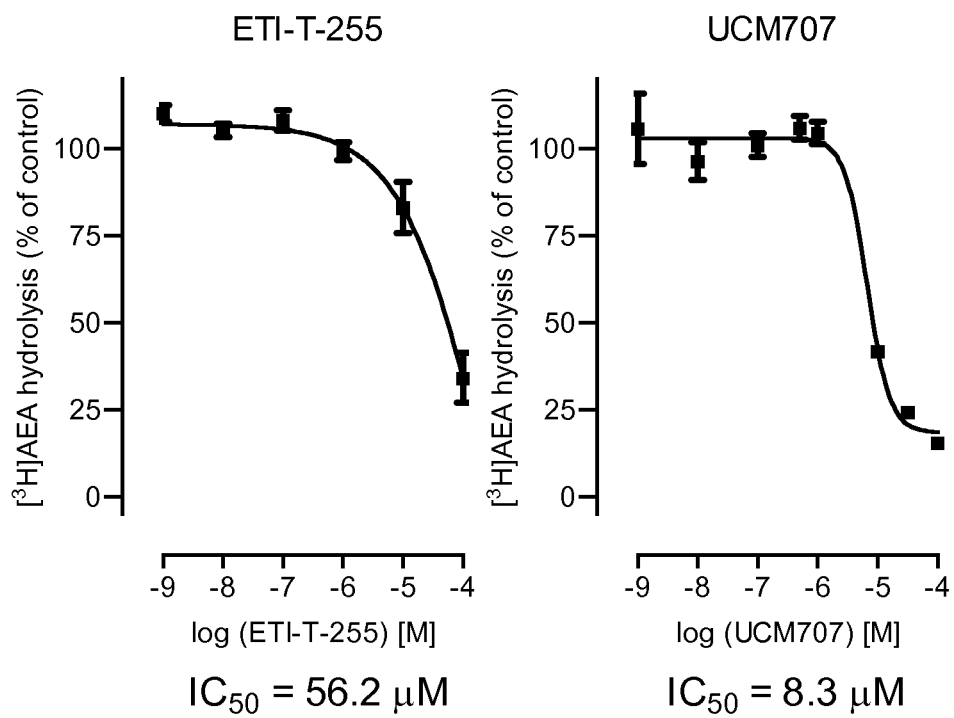
Figure 4:
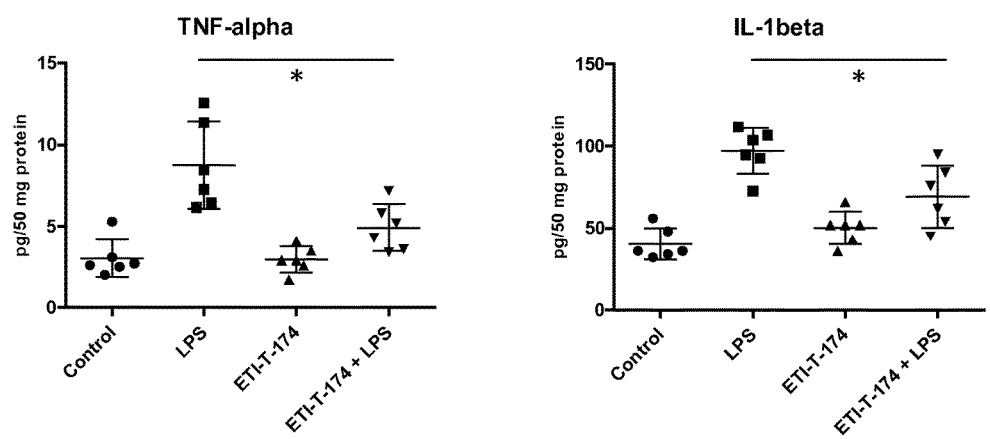
Figure 5:
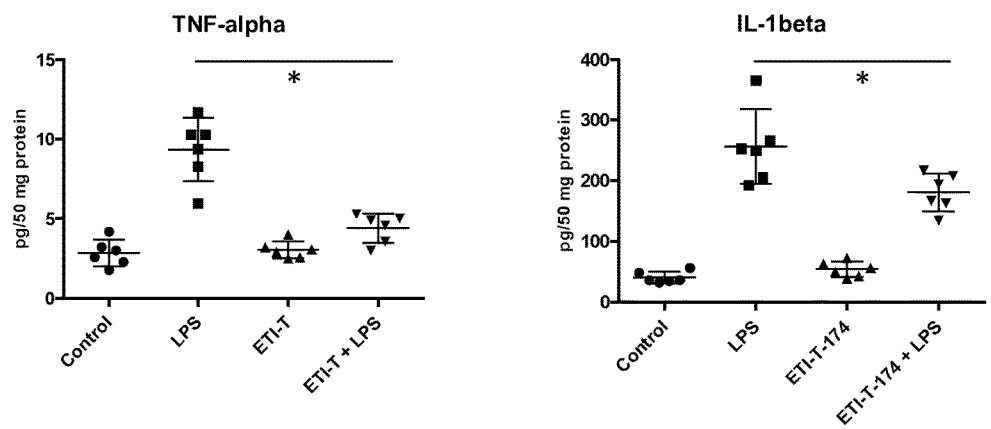

The compounds of the invention are potent inhibitors of AEA cell membrane uptake (FIG. 1) and do not inhibit the AEA metabolic enzyme FAAH (FIG. 2). The compounds of the invention show both cannabimimetic behavioral effects (FIG. 3) and antiinflammatory effects, in particular an antineuroinflammatory effect, as exemplified in the experimental section (FIGS. 4 and 5).

The use of the compounds of the invention in a method for treatment of psychiatric or neurological disorders is related to attenuation of neuroinflammation and neuronal retrograde signaling mediated via endocannabinoids including AEA. Such diseases include bipolar diseases, schizophrenia, sleeping disorders, multiple sclerosis and Alzheimers disease (Ashton and Moore Acta Psychiatr Scand. 2011, 124, 250-61.; Aso and Ferrer I, Front Pharmacol. 2014, 5:37.; Correa et al. Vitam Horm. 2009, 81, 207-30.)

In some embodiments, the compounds of the general formula (1) may be isolated in form of salts, in particular in form of pharmaceutically acceptable salts. The same applies to all of the before mentioned embodiments. In some embodiments, the compounds of the general formula (1) may be isolated in form of a tautomer, a hydrate or a solvate.

Such salts are formed, for example, as acid addition salts, preferably with organic or inorganic acids, from compounds of the general formula (1) with a basic nitrogen atom, in particular the pharmaceutically acceptable salts are formed in such a way. Suitable inorganic acids are, without being limited to, halogen acids, such as hydrochloric acid, sulfuric acid, or phosphoric acid and the like. Suitable organic acids are, without being limited to, carboxylic, phosphonic, sulfonic or sulfamic acids and the like. Such organic acids may be, without being limited to, acetic acid, glycolic acid, lactic acid, malic acid, tartaric acid, or citric acid. Salts may also be formed, for example, as salts with organic or inorganic bases, from compounds of the general formula (1) with a nitrogen atom bearing an acidic hydrogen. Examples of suitable cations are—without being limited to—sodium, potassium, calcium or magnesium cations, or cations of organic nitrogen bases, e.g. protonated mono-, di- or tri-(2-hydroxethyl)amine.

In view of the close relationship between the novel compounds in their free form and those in the form of their salts, any reference to the free compounds hereinbefore and hereinafter is to be understood as referring also to the corresponding salts, as appropriate and expedient. Likewise, in view of the close relationship between the novel compounds of the general formula (1) and their tautomers, any reference to the compounds of the general formula (1) is to be understood as referring also to the corresponding tautomers. The same applies to a hydrate or a solvate.

In some embodiments, the pharmaceutical preparation comprises at least one compound according to the invention as an active ingredient and at least one pharmaceutically acceptable carrier. In some embodiments, the pharmaceutical preparation comprises at least one compound according to the invention in its free form as an active ingredient. In some embodiments, the pharmaceutical preparation comprises at least one compound according to the invention in its free form as an active ingredient and at least one pharmaceutically acceptable carrier.

In some embodiments, the pharmaceutical preparation comprises at least one compound according to the invention in form of a salt, a tautomer, a pharmaceutically acceptable salt, a hydrate or a solvate. In some embodiments, the pharmaceutical preparation comprises at least one compound according to the invention in form of a salt, a tautomer, a pharmaceutically acceptable salt, a hydrate or a solvate and at least one pharmaceutically acceptable carrier.

Furthermore the invention relates to pharmaceutical preparations comprising at least one compound mentioned herein before as active ingredient, which can be used especially in the treatment of the diseases mentioned. The pharmaceutical preparations may be used in particular for a method for treatment of psychiatric disorders.

In some embodiments, the pharmaceutical preparations is for enteral administration, such as nasal, buccal, rectal, local or, especially, oral administration, and for parenteral administration, such as intravenous, intramuscular or subcutaneous administration, are especially preferred. The preparations comprise the active ingredient alone or, in particular, together with a pharmaceutically acceptable carrier. The dosage of the active ingredient depends upon the disease to be treated and upon the species, its age, weight, and individual condition, the individual pharmacokinetic data, and the mode of administration. In particular, the oral application of the active ingredient is preferred.

In some embodiments, the pharmaceutical preparations comprise from approximately 1% to approximately 95% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.005 g to about 1.0 g active ingredient.

In some embodiments, the pharmaceutical preparations of the present invention are prepared in a manner known per se, for example by means of conventional mixing, granulating, coating, dissolving or lyophilizing processes.

In some embodiments, the pharmaceutical preparations is in form of solutions of the active ingredient, and also suspensions or dispersions, especially isotonic aqueous solutions, dispersions or suspensions which, for example in the case of lyophilized preparations comprising the active ingredient alone or together with a carrier, for example mannitol, can be made up before use.

In some embodiments, the pharmaceutical preparations may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

In some embodiments, the pharmaceutical preparation comprises suspensions in oil, which comprise as the oil component a vegetable, synthetic, or semi-synthetic oils customary for injection purposes. In some embodiments, the pharmaceutical preparation comprises a mixtures of fatty acid esters, vegetable oils such as, without being limited to, cottonseed oil, almond oil, olive oil, castor oil, sesame oil, soybean oil and groundnut oil. The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinyl pyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

In some embodiments, the pharmaceutical preparation is suitable for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy ethylene sorbitan fatty acid ester type, may also be added.

In some embodiments, the pharmaceutical preparation is suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

In some embodiments, the pharmaceutical preparation is suitable for parenteral administration, aqueous solutions of an active ingredient in water-soluble form or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. Preferred preservatives are, for example, antioxidants, such as ascorbic acid, or microbicides, such as sorbic acid or benzoic acid.

Particular embodiments of the invention are the compounds:

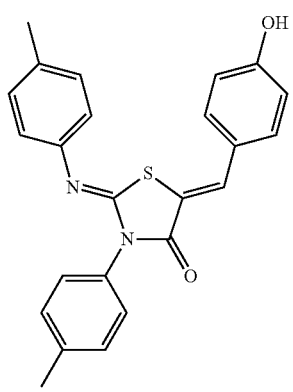 [SMILES: Cc1ccc(/N=C2\S/C(=C\c3ccc(O)cc3)C(=O)N2c2ccc(C)cc2)cc1]

Compound 1

(*ETI-T-351)

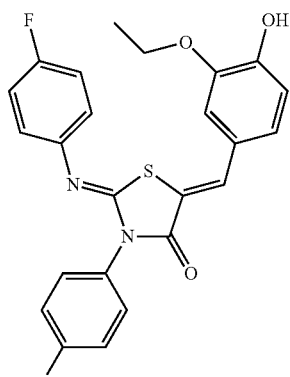

Compound 2

(*ETI-T-255)

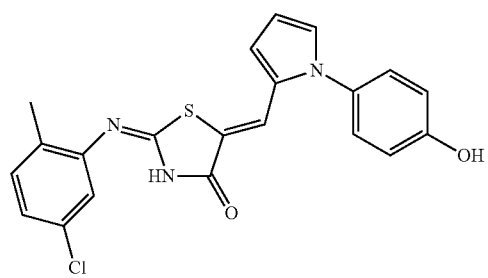

Compound 3

(*ETI-T-045)

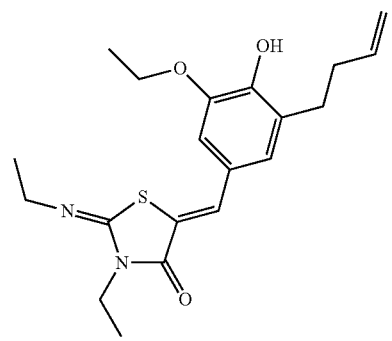 [SMILES: C=CCCc1cc(/C=C2\SC(=NCC)N(CC)C2=O)cc(OCC)c1O]

Compound 4

(*ETI-T-424)

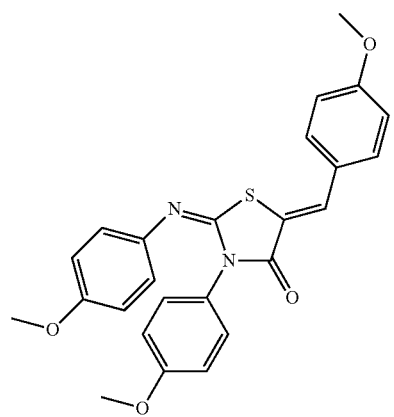

Compound 5

(*ETI-T-174)

Compound 6
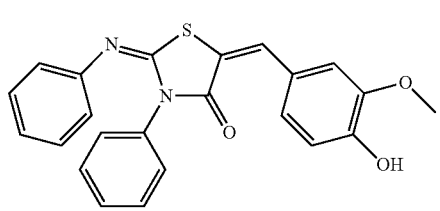
(*ETI-T-348)
Compound 7
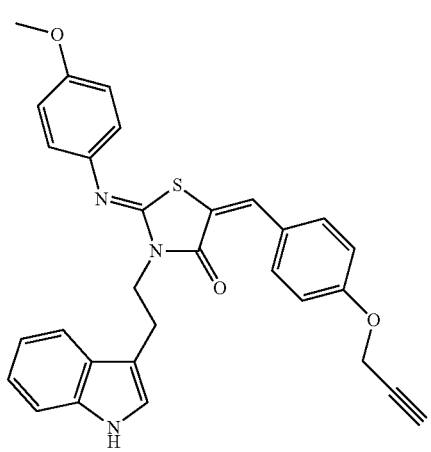
(*ETI-T-365)
Compound 8
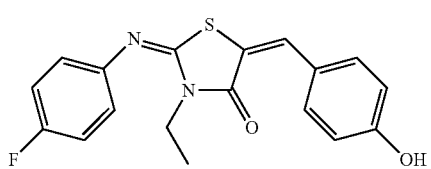
(*ETI-T-413)
Compound 9
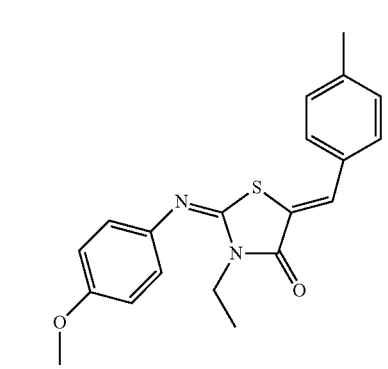
(*ETI-T-874)
Compound 10
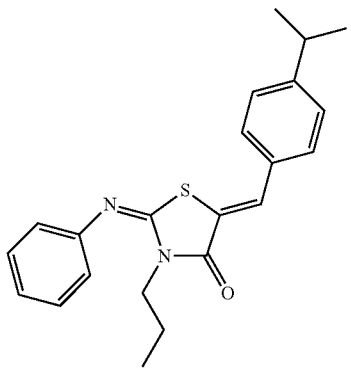
(*ETI-T-395)
Compound 11
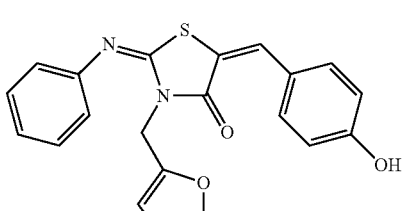
(*ETI-T-193)
Compound 12
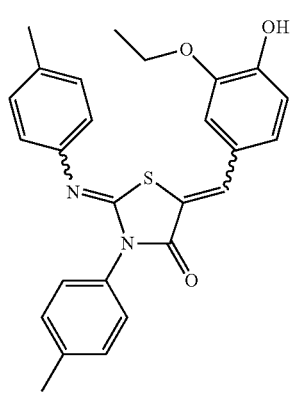 [SMILES: CCOc1cc(/C=C2\S/C(=N\c3ccc(C)cc3)N(c3ccc(C)cc3)C2=O)ccc1O]
(*ETI-T-340)
Compound 13
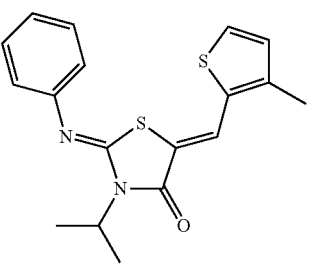 [SMILES: Cc1ccsc1/C=C1\S/C(=N\c2ccccc2)N(C(C)C)C1=O]
(*ETI-T-643)

Compound 14
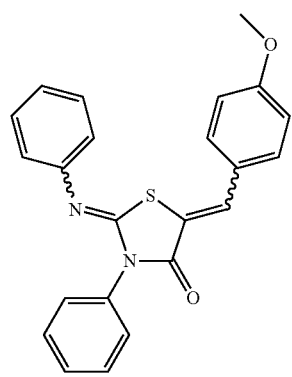 [SMILES: COc1ccc(/C=C2\S/C(=N\c3ccccc3)N(c3ccccc3)C2=O)cc1]
(*ETI-T-339)
Compound 15
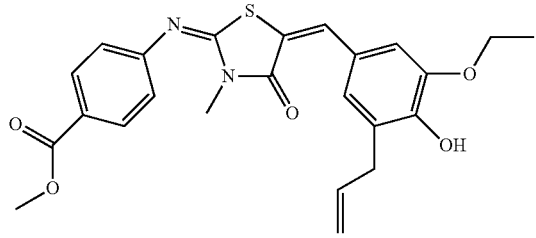
(*ETI-T-357)
Compound 16
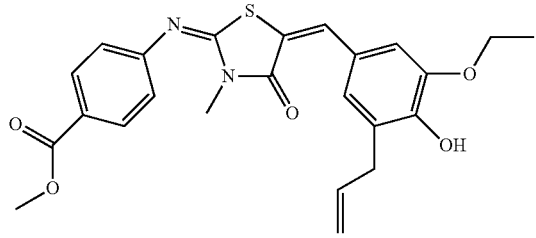
(*ETI-T-390)
Compound 17
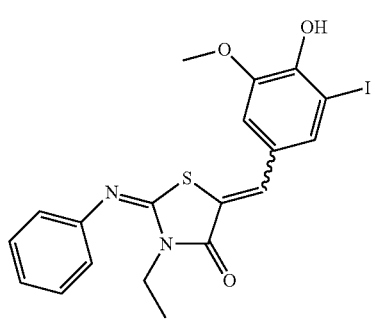
(*ETI-T-396)
Compound 18
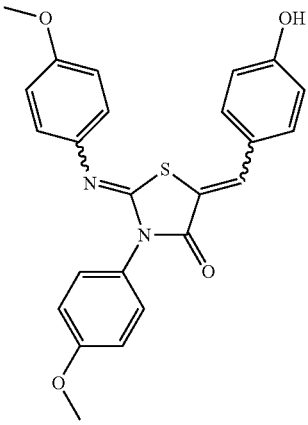 [SMILES: COc1ccc(/N=C2\S/C(=C\c3ccc(O)cc3)C(=O)N2c2ccc(OC)cc2)cc1]
(*ETI-T-347)
Compound 19
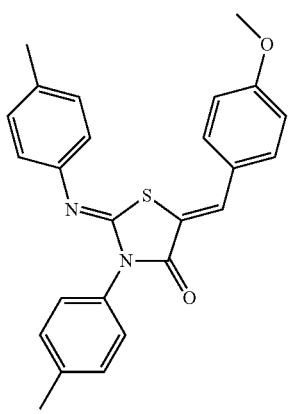 [SMILES: COc1ccc(/C=C2\S/C(=N\c3ccc(C)cc3)N(c3ccc(C)cc3)C2=O)cc1]
(*ETI-T-356)
Compound 20
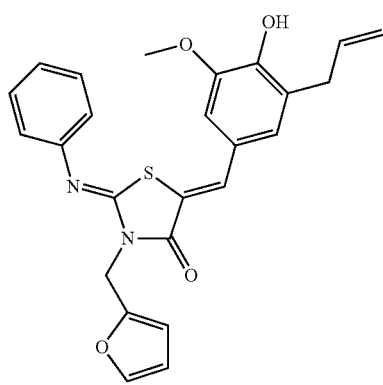 [SMILES: C=CCc1cc(/C=C2\S/C(=N\c3ccccc3)N(Cc3ccco3)C2=O)cc(OC)c1O]
(*ETI-T-198)

-continued
Compound 21
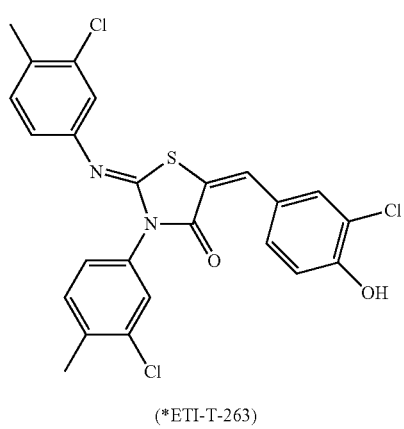
(*ETI-T-263)
Compound 22
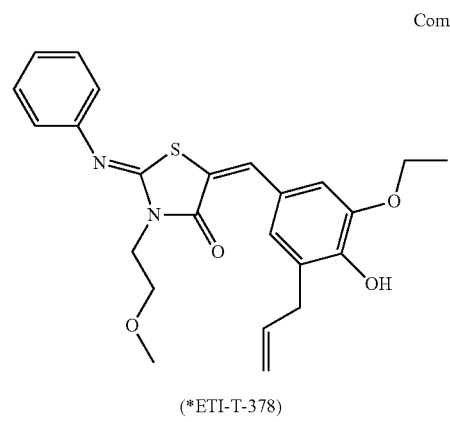
(*ETI-T-378)
Compound 23
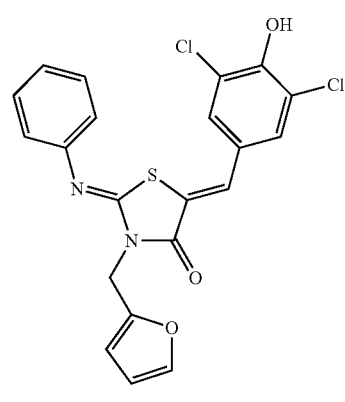
(*ETI-T-209)
Compound 24
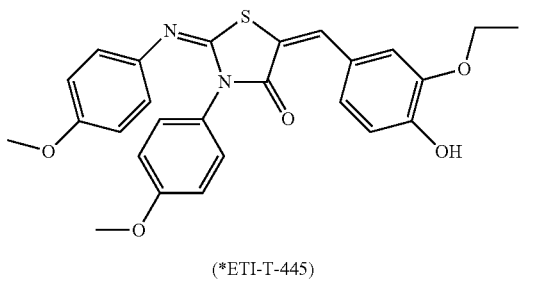
(*ETI-T-446)
Compound 25
(*ETI-T-445)
Compound 26
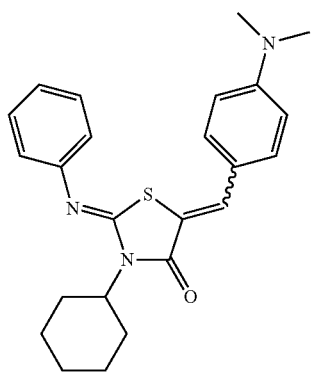 [SMILES: CN(C)c1ccc(/C=C2\S/C(=N\c3ccccc3)N(C3CCCCC3)C2=O)cc1]
(*ETI-T-385)
Compound 27
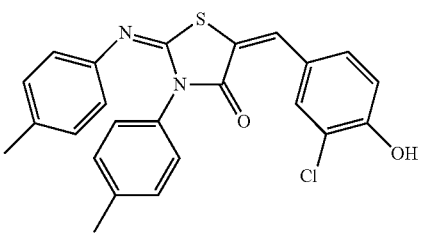
(*ETI-T-444)
Compound 28
(*ETI-T-008)

Compound 29
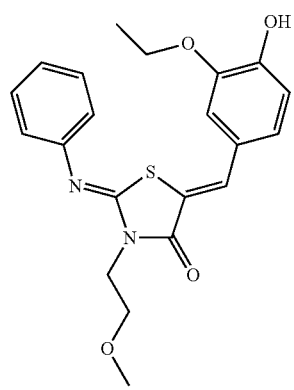 [SMILES: CCOc1cc(/C=C2\S/C(=N\c3ccccc3)N(CCOC)C2=O)ccc1O]
(*ETI-T-410)
Compound 30
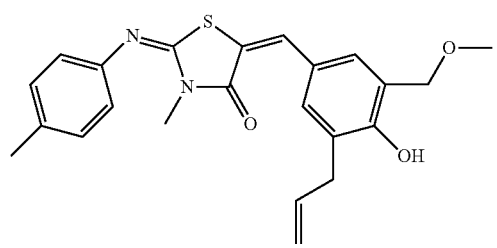
(*ETI-T-399)
Compound 31
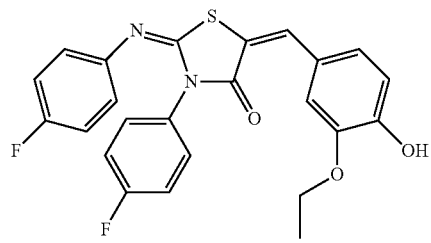 [SMILES: CCOc1cc(/C=C2/S/C(=N/c3ccc(F)cc3)N(c3ccc(F)cc3)C2=O)ccc1O]
(*ETI-T-438)
Compound 32
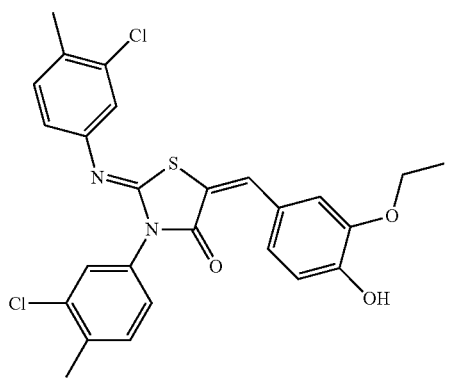 [SMILES: CCOc1cc(/C=C2/S/C(=N\c3ccc(C)c(Cl)c3)N(c3ccc(C)c(Cl)c3)C2=O)ccc1O]
(*ETI-T-435)
Compound 33
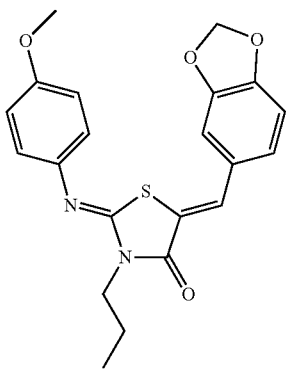 [SMILES: CCCN1C(=O)/C(=C/c2ccc3c(c2)OCO3)S/C1=N\c1ccc(OC)cc1]
(*ETI-T-426)
Compound 34
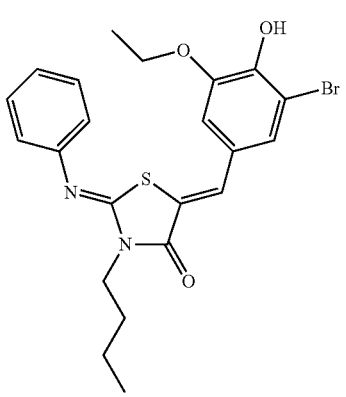 [SMILES: CCCCN1C(=O)/C(=C/c2cc(Br)c(O)c(OCC)c2)S/C1=N\c1ccccc1]
(*ETI-T-401)
Compound 35
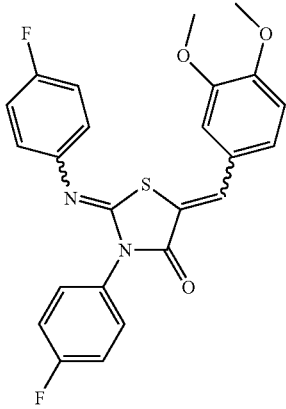 [SMILES: COc1ccc(C=C2SC(=Nc3ccc(F)cc3)N(c3ccc(F)cc3)C2=O)cc1OC]
(*ETI-T-343)

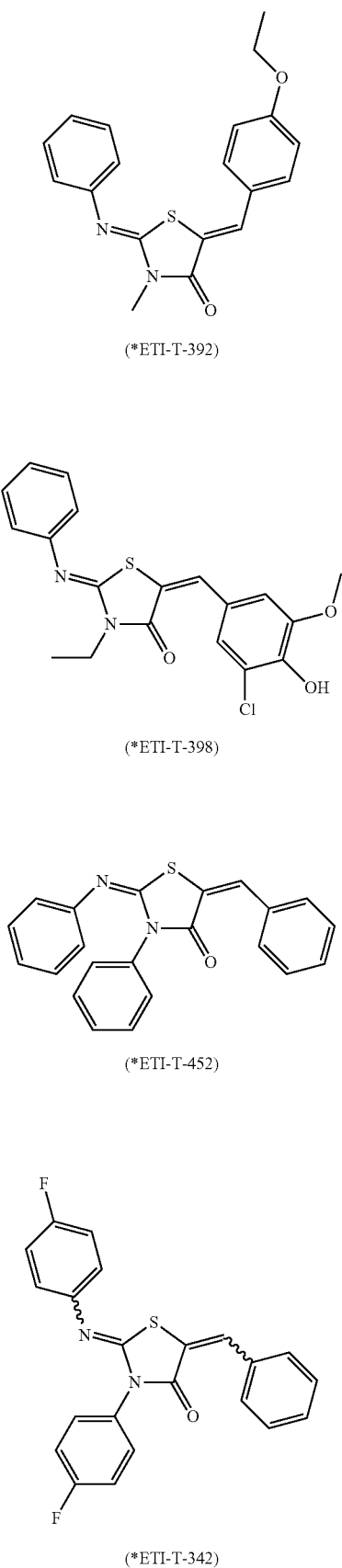

Compound 36
(*ETI-T-392)

Compound 37
(*ETI-T-398)

Compound 38
(*ETI-T-452)

Compound 39
(*ETI-T-342)

Compound 40
(*ETI-T-397)

SHORT DESCRIPTION OF THE FIGURES

FIG. 1: AEA uptake inhibition exemplified by ETI-T-351 (compound 1) and ETI-T-255 (compound 2) vs. positive control UCM707 ((5Z,8Z,11Z,14Z)—N-(3-Furanylmethyl)-5,8,11,14-eicosatetraenamide). Data show mean values of independent experiments ±SEM.

FIG. 2: Lack of FAAH inhibition exemplified by ETI-T-255 (compound 2) and UCM707. Data show mean values of independent experiments ±SEM.

FIG. 3: Cannabimimetic behavioral effects exemplified by compounds ETI-T-174 (compound 5), ETI-T-348 (compound 6), and ETI-T-209 together with reference substances in the tetrad test in BALB/c mice in (A), (B) and (C) respectively. Data show a decreased body temperature for all three compounds, an increased time spent in the immobile state particularly for ETI-T-174 and ETI-T-209, a reduced locomotion particularly for ETI-T-174 and ETI-T-348, an anti-nociceptive effect in the hot plate test for all three compounds tested. OMDM-2 ((R)—N-oleoyl Tyrosinol) and Haloperidol (4-[4-(4-Chlorphenyl)-4-hydroxypiperidino]-4-fluorbutyrophenon) were used as positive controls, in (D) and (E) respectively. If not indicated else the results were compared vs. vehicle (CTRL). * P<0.001,  P<0.01, * P<0.05, ns=not significant P>0.05.

FIG. 4 Acute anti-inflammatory effect exemplified by compound ETI-T-174 in BALB/c mice on TH1 cytokines TNF-alpha and IL-1beta in brain upon endotoxemia. Decrease of the pro-inflammatory TNF-alpha and IL-1beta levels in total brain after 2 hours upon ETI-T-174 treatment. (5 mg/kg, i.p. of ETI-T-174) was administered 30 min prior to challenge with LPS (250 µg/100 g, i.p.). Data are mean values±S.D. and the results were compared to vehicle (control). * P<0.05.

FIG. 5 Long term anti-inflammatory effect exemplified by compound ETI-T-174 in BALB/c mice on TH1 cytokines TNF-alpha and IL-1beta in brain upon endotoxemia. Decrease of the pro-inflammatory TNF-alpha and IL-1beta levels in total brain after 8 hours upon ETI-T-174 treatment. (5 mg/kg, i.p. of ETI-T-174) was administered 30 min prior to challenge with LPS (250 µg/100 g, i.p.). Data are mean values±S.D. and the results were compared to vehicle (control). * P<0.05.

GENERAL METHODS AND MATERIALS

Compounds and chemicals were of purest possible grade. Anandamide (AEA), (R)—N-(1-(4-hydroxyphenyl)-2-hydroxyethyl)oleamide (OMDM-2), N-(3-furanylmethyl)-(5Z,8Z,11Z,14Z)-eicosatetraenamide (UCM707), (3-aminocarbonyl)[1,1-biphenyl]-3-yl)-cyclohexylcarbamate (URB597), (R)-(+)-[2,3-Dihydro-5-methyl-3-(4-morpholinylmethyl)pyrrolo[1,2,3-de]-1,4-benzoxazin-6-yl]-1-naphthalenyl methanone mesylate (R-(+)-WIN55,212-2) were purchased from Tocris Bioscience. CP55,940 [side chain-2, 3,4-3H(N)] (144 Ci/mmol) was ordered from PerkinElmer. [ethanolamine-1-3H]-AEA (60 Ci/mmol) was purchased from American Radiolabeled Chemicals. Albumin from bovine serum essentially fatty acid free (BSA) (A7030), fetal bovine serum (F7524), RPMI-1640 and LPS (E. coli 055:B5) were purchased from Sigma-Aldrich, Germany. AquaSil™ siliconizing fluid was purchased from Thermo Scientific. Haloperidol (Haldol®) was purchased as injectable solution of 5 mg/mL from Janssen-Cilag, Switzerland.

[$^3$H]-AEA Cellular Uptake

Screening for AEA cellular uptake inhibition was performed in a semi-automated procedure: Pipetting and washing steps were performed by a Biomek3000 laboratory workstation. First, required amounts of U937 cells were centrifuged at 100×g for 5 min and resuspended in RPMI (37° C.) to a final concentration of $2 \times 10^6$ cells/mL. Then, 250 μL of cell suspension ($0.5 \times 10^6$ cells per sample) were transferred into AquaSil™ silanized glass vials (Chromacol 1.1-MTV) in 96-well format. After addition of 5 μL vehicle (DMSO) or compounds the cells were incubated at 37° C. for 15 min. As positive controls OMDM-2 and UCM707 were used at 10 μM in each run. The ETI-T compounds were measured at up to 7 concentrations in triplicates from 100 pM-100 μM. After pre-incubation, a mixture of 0.5 nM[ethanolamine-1-$^3$H]-AEA, (60 Ci/mmol) and 99.5 nM of cold AEA (final 100 nM) was added and samples were incubated at 37° C. for another 15 min. The reaction was stopped by rapid filtration over UniFilter-96 GF/C filters (PerkinElmer) pre-soaked with PBS 0.25% BSA. Cells were washed three times with 100 μL ice-cold PBS buffer containing 1% fatty acid free BSA. After drying, 45 μL MicroScint 20 scintillation cocktail (PerkinElmer, Waltham, Mass., US) was added to the wells and the plate was sealed. Radioactivity was measured by liquid scintillation counting on a PerkinElmer Wallac Trilux MicroBeta 1450 during 2 min. Non-specific binding of [$^3$H]AEA (100 nM) to the glass vials was never higher than 10%. $IC_{50}$ values were calculated by GraphPad® by non-linear regression using the built-in log (inhibitor) vs. response-variable slope (four parameters) function.

FAAH Activity

Hydrolysis of [$^3$H]-AEA by FAAH was determined as previously described in cell homogenates of U937 cells (0.18 mg protein) (Omeir et al., 1999, Biochem Biophys Res Commun, 264, 316-20; Mor et al., 2004, J Med Chem, 47, 4998-5008). Protein amounts of cell homogenates corresponded to $0.5 \times 10^6$ cells (U937), to assure best possible comparability of $IC_{50}$ values as used for the AEA cellular uptake assays. URB597 was used as positive control. Protein quantification was performed using a BCA assay (Thermo Scientific). Enzyme activity was assessed by addition of vehicle or compounds in 10 μL DMSO to 490 μL homogenate in 10 mM Tris HCl, 1 mM EDTA, 0.1% (w/v) BSA fatty acid free, pH=8 and incubation for 15 min at 37° C. After, a mixture of AEA plus [ethanolamine-1-$^3$H]-AEA (0.5 nM) at final 100 nM was added to the homogenates and incubated for 15 min at 37° C. The reaction was stopped by addition of 1 mL ice-cold CHCl$_3$:MeOH (1:1) followed by vigorous vortexing. Phase separation was achieved by centrifugation at 10'000×g at 4° C. for 10 min. Radioactivity of the separated aqueous phase (upper phase) containing [$^3$H-ethanolamine] or [$^3$H-glycerol] was measured by liquid scintillation counting on a Tri-Carb 2100 TR liquid scintillation analyzer after addition of 3.5 mL Ultima Gold scintillation cocktail (PerkinElmer Life Sciences). Results are expressed as hydrolysis of tritium substrate in percent of vehicle treated control. $IC_{50}$ values were calculated by GraphPad®. Data are reported as means of n=3 independent experiments performed in triplicates.

Membrane Preparation

Stably transfected CHO-K1 cells expressing $hCB_1$ or $hCB_2$ receptors (Gertsch et al., 2008, Proc Natl Acad Sci 105, 9099-104) were cultured in T150 cm$^2$ flasks up to 90% confluence. The medium was removed and cells were washed twice with PBS, 37° C. 10 mL of PBS was added and the cells were scraped and transferred into a falcon tube following homogenization by a Polytron PT1300D for 5 min at 30 krpm. Then, the homogenate was centrifuged (1400×g, 5 min) to remove debris. The supernatant was subjected to ultracentrifugation (64000×g, 45 min, 4° C.) to separate cytosolic from the membrane fraction. The supernatant was discharged and the pellet resuspended in PBS by sonication. Protein quantity was determined by BCA assay (Thermo Scientific) and aliquots of 500 μL were stored at −80° C. until use.

Radioligand CB Receptor Binding

Binding properties of ETI-T compounds to hCB1 or $hCB_2$ receptors were performed as previously reported in a [$^3$H]-CP55,940 displacement assay (Gertsch et al., 2008, Proc Natl Acad Sci 105, 9099-104). WIN 55,212-2 was used as positive control. In brief, 20 μg protein of CHO-K1 $hCB_1$ or $hCB_2$ membrane preparations were thawed on ice and resuspended in a final volume of 500 μL binding buffer (50 mM Tris-HCl, 2.5 mM EDTA, 5 mM MgCl2, 0.5% fatty acid free BSA, pH 7.4) in silanized glass vials. [$^3$H]-CP55, 940 (168 Ci/mmol) (PerkinElmer, Waltham, Mass., US) was added to a final concentration of 0.5 nM followed by the addition of competitors or vehicle in 5 μL DMSO. Membrane binding was equilibrated for 2 h at room temperature (25° C.). Samples were filter through a 0.1% polyethylenimine pre-soaked UniFilter®-96 GF/B plate (PerkinElmer) and washed twelve times with 167 μL ice-cold assay-buffer. The plate was dried, bottom sealed and 45 μL MicroScint 20 scintillation cocktail (PerkinElmer) were added before measured on a PerkinElmer 1450 Microbeta TRILUX liquid scintillation counter. Unspecific binding was determined by WIN 55,212-2, 10 μM and subtracted from all values. $IC_{50}$ values expressing.

In vivo Tetrad Test in BALB/c Mice

In mice cannabimimetic substances induce a characteristic profile of behavioral effects (tetrad) which include suppression of locomotion, antinociception, hypothermia and catalepsy (Martin et al., 1991, Pharmacol Biochem Behav, 40, 471-8; Wiley, 2003, Eur J Pharmacol, 471, 185-93; Howlett et al., 2002, Pharmacol Rev, 54, 161-202). Male BALB/c mice (8 weeks old, 20-25 g body weight) were housed under standard environmental conditions (n=5 per cage) at 22-24° C. under a 12 h to 12 h light-dark cycle supplied with food and water ad libitum. ETI-T compounds were dissolved in pure DMSO and administered intraperitoneally (i.p) at doses of 5.0 mg/kg in 20 μL of vehicle 60 min prior to evaluation of behavioural effects. The tetrad test battery was carried out as follows: Rectal temperature was determined using a Physitemp thermometer (Physitemp Instruments Inc., Clifton, N.J. with a thermocoupled probe 1-2 cm into the rectum. The temperature was measured 10 min before compound administration and 1 h post injection. Changes in rectal temperature were expressed as the difference between basal and post injection temperatures. Catalepsy was determined using the bar test where mice were placed on a bar oriented parallel to and approximately 4-5 cm off of the ground. The duration of the time a mouse remained motionless (except respiration) with its front paws on the bar was scored over 40 s. Hypomotility was determined using the RotaRod performance test based on a rotating rod with forced motor activity being applied to the mouse. The maximal duration of this test was about 120 s at a velocity of 4 rpm. Analgesia was determined by the hot plate test. Mice were place on a heated plate (54-56° C.) in a Plexiglas cylinder for a maximum of 2 min. The time until the mouse showed the specific flexor or antialgesic reflex response was measured and the mouse was immediately removed. All experiments were repeated independently on different days. Animals were handled according to the guidelines on use and care of experimental animals (Mexican Official Norm NOM-062-ZOO-1999 published by SAGARPA in the Diario Oficial del Gobierno Mexicano, 2001), which is in accordance with the Code of Ethics of the Directive 2010/63/EU.

Endotoxemia Mouse Model

Male BALB/c mice were injected i.p. with test compounds (5 mg/kg) or vehicle (DMSO, 20 μL) 30 min prior to LPS administration (250 μg/100 g body weight) in 50 μL saline solution. The administrations were conducted between 9:00 and 10:00 am. 30 min prior to scarification, 20 units (200 μL) of Inhepar® were injected subcutaneously. 1 h after LPS administration all animals were anesthetized with ether and sacrificed by intracardial puncture. The brain was immediately removed on ice and stored in liquid nitrogen. DMSO showed marginal stimulation of cytokines. The concentrations of the cytokines in brain and plasma were measured using commercially available Luminex MagPix cytokines assay (BioRad) specific for mice, according to the manufacturer's instructions. The acquisition of the fluorescent signal was achieved by a charged-coupled device (CCD) imager. The concentration of the analytes was determined by MAGPIX xPONENT. The assays were run in triplicates and the concentrations were expressed in pg/mL based on a standard curve.

Statistical Analysis

Statistical analysis and $IC_{50}$ values were determined using GraphPad® Prism 5.0 (GraphPad® Software, San Diego, Calif., US). Inhibition curves were obtained by non-linear regression using the built-in log(inhibitor) vs. response-variable slope (four parameters) function. Results were calculated as % of vehicle control of the corresponding fraction (cells, aqueous phase) if not mentioned else. In vivo results are shown in absolute values and were analyzed by a one-way ANOVA following a Tukey's multiple comparison test or student's t-test. If not indicated else the results were compared vs. vehicle (CTRL). * P<0.001,  P<0.01, * P<0.05, ns=not significant P>0.05.

General Synthesis

The compounds of the invention may be produced according to one of the pathways depicted in scheme 1 or scheme 2. The starting materials may be purchased or produced according to literature procedures.

Scheme 1: a) solvent, optional a base; b) $R^1$—CH=O, piperidine, EtOH, 18 h or 2 eq. NaOH, AcOH, 60-110° C., 3-24 h (analogue to J.Med.Chem.; 2010; 53 (10), 4198 or J.Med.Chem.;2008; 51, 1242), with R being H, methyl or ethyl and LG being a leaving group such as Cl or Br.

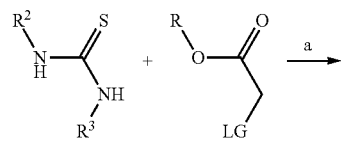

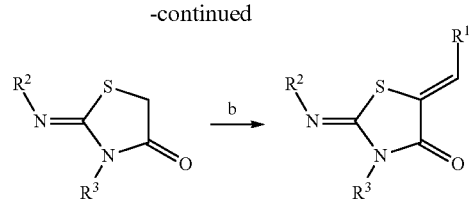

Scheme 2: a) solvent, base; b) $R^1$—CH=O, piperidine, EtOH, 18 h or 2 eq. NaOH, AcOH, 60-110° C., 3-24 h (analogue to J.Med.Chem.; 2010; 53 (10), 4198 or J.Med.Chem.;2008; 51, 1242).

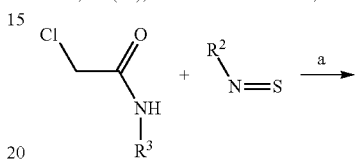

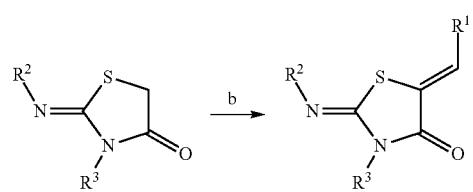

Evaluation:

TABLE 1

AEA uptake inhibition of ETI-T compounds

| Compound | AEA uptake inhibition IC50 (μM) |
| --- | --- |
| 1 | 0.068 |
| 2 | 0.074 |
| 3 | 0.138 |
| 4 | 0.145 |
| 5 | 0.148 |
| 6 | 0.225 |
| 7 | 0.266 |
| 8 | 0.268 |
| 9 | 0.334 |
| 10 | 0.355 |
| 11 | 0.434 |
| 12 | 0.484 |
| UCM707 | 1.9 |
| 13 | 0.510 |
| 14 | 0.542 |
| 15 | 0.553 |
| 16 | 0.571 |
| 17 | 0.594 |
| 18 | 0.597 |
| 19 | 0.602 |
| 20 | 0.661 |
| 21 | 0.798 |
| 22 | 0.899 |
| 23 | 0.990 |
| OMDM-2 | 3.9 |

Besides their new chemical scaffold the ETI-T AEA uptake inhibitors show a higher potency in AEA uptake inhibition than the current reference inhibitors UCM707 and OMDM-2 (Tab 1.). Simultaneously, the ETI-T AEA uptake show a higher selectivity than UCM707 or OMDM-2 over FAAH, which is the main off-target that has to be taken into account during AEA uptake inhibition (Tab. 2) (Fowler et al., 2004, Eur J Pharmacol, 492, 1-11). I. e. compound 2 (ETI-T-255, see Figures) shows an apparent selectivity for AEA uptake inhibition over FAAH inhibition of ~760-fold, while UCM707 or OMDM-2 show only a selectivity of 4 to 6-fold.

TABLE 2

Negligible effect of selective ETI-T compounds on FAAH inhibition

| Compound | FAAH inhibition IC50 (µM) |
|---|---|
| 2 | 56.2 |
| 12 | >100 |
| UCM707 | 8.3 |
| 16 | >100 |
| 23 | 60.3 |
| OMDM-2 | 23.4 |

TABLE 3

Effect of selective ETI-T compounds on CB1 receptor binding

| Compound | CB1 receptor binding % binding at 10 µM |
|---|---|
| 2 | 33 |
| 12 | 35 |
| 16 | 15 |
| 23 | 24 |

Acting exclusively as indirect CB1 receptor agonists, the ETI-T compounds do not bind to the CB1 receptor. Shown in Tab. 3, no relevant CB1 receptor interaction is present for the ETI-T compounds, which substantiates their high selectivity for AEA uptake inhibition. For comparison reasons, the Ki values of the reference substances UCM707 and OMDM-2 are Ki>1 µM and Ki=5.1 µM respectively (Ortar et al., 2003, Biochem Pharmacol, 65, 1473-81 and López-Rodriguez et al., 2001, J Med Chem, 44:4505-8).

Further results are shown in table 4 below:

| ETI-T-compound | AEA uptake IC50 (µM) | FAAH inhibition IC50 (µM) | CB1 receptor binding (% at 10 µM) |
|---|---|---|---|
| 351 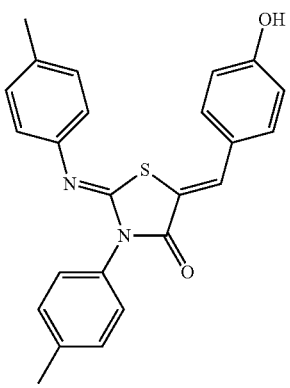 | 0.068 | | 33 |
| 255 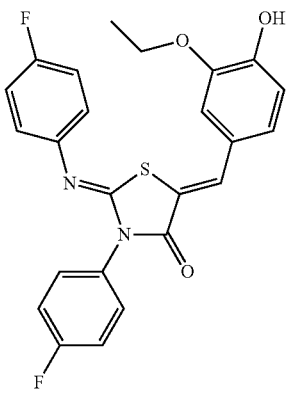 | 0.074 | 56.2 | 33 |

-continued

| ETI-T-compound | AEA uptake IC50 (μM) | FAAH inhibition IC50 (μM) | CB1 receptor binding (% at at 10 μM) |
|---|---|---|---|
| 424 | 0.145 | | |
| 174 | 0.148 | 20.4 | 37 |
| 348 | 0.225 | 26.915 | 64 |

| ETI-T-compound | AEA uptake IC50 (μM) | FAAH inhibition IC50 (μM) | CB1 receptor binding (% at at 10 μM) |
|---|---|---|---|
| 365 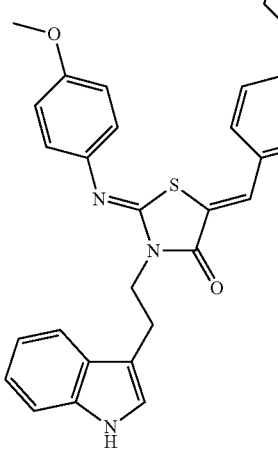 | 0.266 | | |
| 413 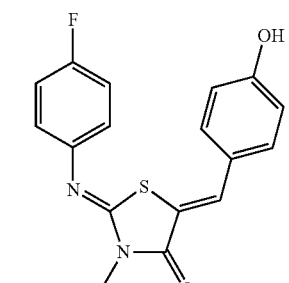 | 0.268 | | |
| 874 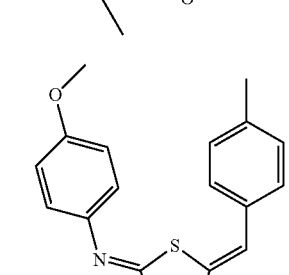 | 0.334 | | |
| 395 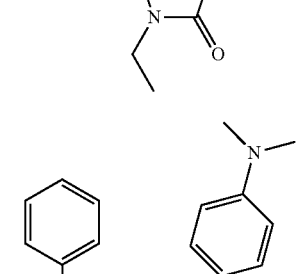 | 0.355 | 1.05 | 29 |

-continued
| ETI-T-compound | AEA uptake IC50 (μM) | FAAH inhibition IC50 (μM) | CB1 receptor binding (% at at 10 μM) |
|---|---|---|---|
| 193 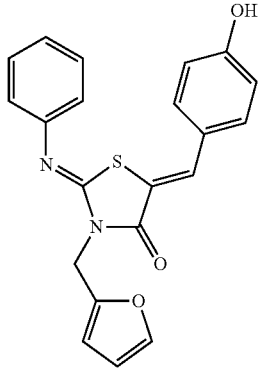 | 0.434 | | |
| 340 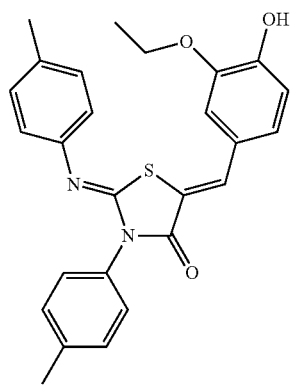 | 0.484 | | 35 |
| 643 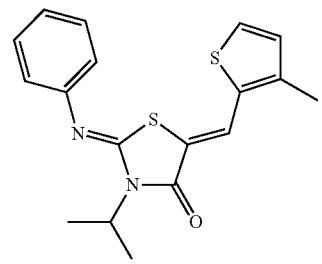 | 0.510 | | |
| 339 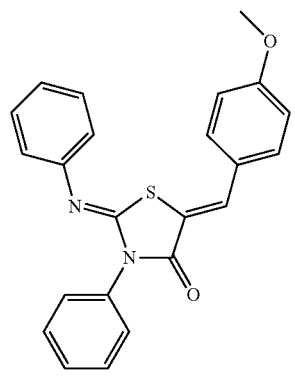 | 0.542 | | |

-continued

| ETI-T-compound | AEA uptake IC50 (μM) | FAAH inhibition IC50 (μM) | CB1 receptor binding (% at at 10 μM) |
|---|---|---|---|
| 357 | 0.553 | | |
| 390 | 0.571 | | 15 |
| 396 | 0.594 | | |
| 347 | 0.597 | | |

-continued

| ETI-T-compound | AEA uptake IC50 (μM) | FAAH inhibition IC50 (μM) | CB1 receptor binding (% at at 10 μM) |
|---|---|---|---|
| 356 | 0.602 | | |
| 198 | 0.661 | | |
| 263 | 0.798 | 58.9 | 45 |
| 378 | 0.899 | >100 | 34 |

-continued

| ETI-T-compound | AEA uptake IC50 (μM) | FAAH inhibition IC50 (μM) | CB1 receptor binding (% at at 10 μM) |
|---|---|---|---|
| 209 | 0.990 | 60.3 | 24 |
| 445 | 1.050 | | |
| 385 | 1.083 | 0.985 | 40 |
| 444 | 1.147 | | |

-continued

| ETI-T-compound | AEA uptake IC50 (μM) | FAAH inhibition IC50 (μM) | CB1 receptor binding (% at at 10 μM) |
|---|---|---|---|
| 008 Jspg | 1.250 | 5.37 | |
| 410 | 1.300 | | |
| 399 | 1.325 | | 41 |
| 438 | 1.350 | | |

| ETI-T-compound | AEA uptake IC50 (μM) | FAAH inhibition IC50 (μM) | CB1 receptor binding (% at at 10 μM) |
|---|---|---|---|
| 435 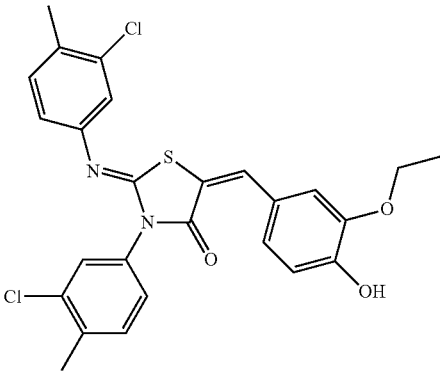 | | 1.427 | |
| 426 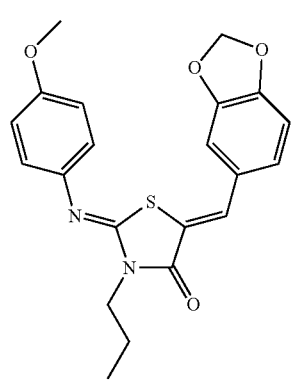 | | 1.459 | 60 |
| 401 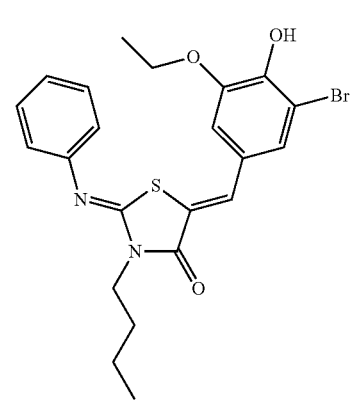 | | 1.577 | 42 |
| 343 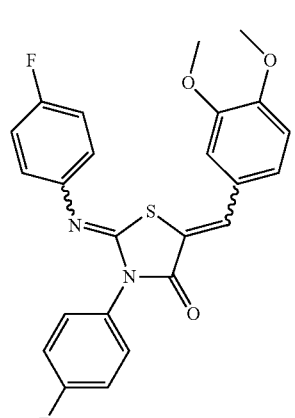 | | 1.590 | |

Particular embodiments of the invention are the compounds shown in the tables 1 to 4.

By inhibiting AEA uptake the ECS can be modulated in a unique way, leading to diverse pharmacological actions like analgesia, anti-inflammatory and CNS effects exemplified by the tetrad effect (Nicolussi & Gertsch, 2015, Vitam Horm. 98:441-85.). The ECS modulating effects of the ETI-T inhibitors is exemplified by its analgesic (FIG. 3) and antiinflammatory effects (FIG. 4). The overall cannabimimetic action is exemplified by the tetrad (FIG. 3).

The invention claimed is:

1. A method for treating neuroinflammation comprising administering a therapeutically effective amount of a compound according to the following formula (1) to a patient in need of such treatment:

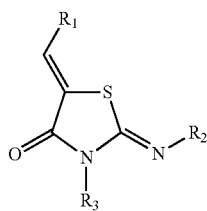

(formula 1)

wherein
$R^1$ represents formula 3

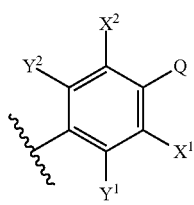

(formula 3)

wherein Q represents
—OH, and
with at least one of $X^1$ or $X^2$ being selected from
—$R^c$ with each $R^c$ being selected from a substituted or unsubstituted $C_1$-$C_8$ alkyl, a substituted or unsubstituted $C_2$-$C_8$ alkenyl, or a substituted or unsubstituted $C_2$-$C_8$ alkynyl, or
—$OR^c$ with each $R^c$ being selected from a unsubstituted $C_3$-$C_4$ alkyl, a substituted or unsubstituted $C_2$-$C_8$ alkenyl, or a substituted or unsubstituted $C_2$-$C_8$ alkynyl, or
F, Br or I, wherein
the other one of $X^1$ or $X^2$ being selected from
F, Cl, Br, I, —$R^c$ or —$OR^c$ or -$NR^c_2$, and with each $R^c$ being selected independently from each other from
H,
a substituted or unsubstituted $C_1$-$C_8$ alkyl,
a substituted or unsubstituted $C_2$-$C_8$ alkenyl, or
a substituted or unsubstituted $C_2$-$C_8$ alkynyl, and with $Y^1$ and $Y^2$ being selected independently from each other from
F, Cl, Br, I, —$R^d$ or —$OR^d$ or —$NR^d_2$, and with each $R^d$ being selected independently from each other from
H,
a substituted or unsubstituted $C_1$-$C_8$ alkyl,
a substituted or unsubstituted $C_2$-$C_8$ alkenyl, or
a substituted or unsubstituted $C_2$-$C_8$ alkynyl, or
or
with at least one of $X^1$ or $X^2$ being selected from F, Cl, Br, or I, and the other one of $X^1$ or $X^2$ being H or F, Cl, Br, or I, and with $Y^1$ and $Y^2$ being selected independently from each other from
F, Cl, Br, I, —$R^d$ or —$OR^d$ or —$NR^d_2$, and with each $R^d$ being selected independently from each other from
H,
a substituted or unsubstituted $C_1$-$C_8$ alkyl,
a substituted or unsubstituted $C_2$-$C_8$ alkenyl, or
a substituted or unsubstituted $C_2$-$C_8$ alkynyl, and
each of $R^2$ and $R^3$ are selected independently from each other from
a substituted or unsubstituted cycloalkyl,
a substituted or unsubstituted aryl,
a substituted or unsubstituted saturated heterocycle, or
a substituted or unsubstituted heteroaryl.

2. The method according to claim 1, wherein the compound comprises a (2Z,5Z), (2Z,5E), (2E,5Z) or (2E,5E) isomer form, or mixtures of the before mentioned isomer forms, characterized by formula 1a

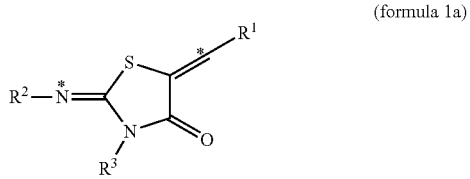

(formula 1a)

with the isomer center being indicated by the asterix (*), with $R^1$, $R^2$ and $R^3$ having the same meaning as defined in claim 1.

3. The method according to claim 1, wherein the compound is an endocannabinoid system modulator.

4. The method according to claim 1, wherein $R^1$ represents formula 3 with $Y^1$ and $Y^2$ are selected independently from each other from
F, Cl, Br or I, or
—$R^d$, with $R^d$ being selected from
H,
a substituted or unsubstituted $C_1$-$C_8$ alkyl,
a substituted or unsubstituted $C_2$-$C_8$ alkenyl, or
a substituted or unsubstituted $C_2$-$C_8$ alkynyl, or
—$OR^d$, with $R^d$ being selected from
H,
a substituted or unsubstituted $C_1$-$C_8$ alkyl, or
a substituted or unsubstituted $C_2$-$C_8$ alkenyl.

* * * * *